(12) United States Patent
Lin et al.

(10) Patent No.: US 9,284,590 B2
(45) Date of Patent: Mar. 15, 2016

(54) MONODISPERSE RANDOM COIL PROTEINS AND BIOCONJUGATES THEREOF

(75) Inventors: Jennifer Sue Lin, Palo Alto, CA (US); Annelise E. Barron, Palo Alto, CA (US); Jennifer Coyne Albrecht, Palo Alto, CA (US); Xiaoxiao Wang, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 257 days.

(21) Appl. No.: 13/327,696

(22) Filed: Dec. 15, 2011

(65) Prior Publication Data
US 2012/0202948 A1  Aug. 9, 2012

Related U.S. Application Data

(60) Provisional application No. 61/423,363, filed on Dec. 15, 2010.

(51) Int. Cl.
| | |
|---|---|
| C12N 15/11 | (2006.01) |
| C07K 1/22 | (2006.01) |
| C12P 21/02 | (2006.01) |
| C07K 14/00 | (2006.01) |
| C12P 21/06 | (2006.01) |
| A61K 38/00 | (2006.01) |

(52) U.S. Cl.
CPC .............. *C12P 21/02* (2013.01); *C07K 14/001* (2013.01); *C12P 21/06* (2013.01); *C07K 2319/21* (2013.01)

(58) Field of Classification Search
CPC ............... C07K 19/00; C07K 2319/21; C07K 2319/20; C07K 1329/00; A61K 38/482
See application file for complete search history.

(56) References Cited

U.S. PATENT DOCUMENTS

| 8,114,599 B2 * | 2/2012 | Meagher et al. ............. 435/6.11 |
| 2005/0037960 A1 * | 2/2005 | Rolke et al. ...................... 514/12 |
| 2005/0202532 A1 * | 9/2005 | Bielicki et al. ............... 435/69.1 |
| 2008/0241950 A1 * | 10/2008 | Meagher et al. ................. 436/94 |
| 2012/0121630 A1 * | 5/2012 | Bryan et al. ............... 424/186.1 |

FOREIGN PATENT DOCUMENTS

WO    WO 2005111068 A2 * 11/2005

OTHER PUBLICATIONS

Banki et al. (Nature Methods (2005) vol. 2, No. 9, pp. 659-661).*
Novagen ( 1995) T7 tag affinity purification kit, pp. 1-5.*
Sigma (2007) Ni-NTA-ATTO Conjugates, www.sigmaaldrich.com/technical-documents/articles/biofiles/ni-nta-atto-conjugates.html, pp. 1-5.*
Liu et al. (1987) Probing the heparin-binding domain of human Antithrombin III with V8 protease, Eur. J. Biochem, vol. 167, pp. 247-252.*
Albrecht et al., "A 265-base DNA sequencing read by capillary electrophoresis with no separation matrix", Anal. Chem., vol. 93, pp. 509-515 (2011).
David et al., "Synthesis and characterization of a new class of cationic protein polymers for multivalent display and biomaterial applications", Biomacromolecules, vol. 10, pp. 1125-1134 (2009).
Farmer et al., "Conformational properties of helical protein polymers with varying densities of chemically reactive groups", Macromolecules, vol. 39, No. 1, pp. 162-170 (2008).
Farmer et al., "Evaluation of Conformation and Association Behavior of Multivalent Alanine-Rich Polypeptides", Pharm. Res., vol. 25, pp. 700-708 (2008).
Haynes et al., "Comblike, monodisperse polypeptoid drag-tags for DNA separations by end-labeled free-solution electrophoresis (ELFSE)", Bioconjugate Chem., vol. 16, No. 4, pp. 929-938 (2005).
Haynes et al., "A chemically synthesized peptoid-based drag-tag enhances free-solution DNA sequencing by capillary electrophoresis", Biopolymers, vol. 96, No. 5, pp. 702-707 (2011).
Huang et al., "Cloning, Expression, and Assembly of Sericin-like Protein", J. Biol. Chem., vol. 278, pp. 46117-46123 (2003).
Kiick et al., "Incorporation of azides into recombinant proteins for chemoselective modification by the Staudinger ligation", Proc. Natl. Acad. Sci., U.S.A., vol. 99, pp. 19-24 (2002).
Kim et al., "A stereoelectronic effect on turn formation due to proline substitution in elastin-mimetic polypeptides", J. Am. Chem. Soc., vol. 127, No. 51, pp. 18121-18132 (2005).
Lin et al., "Completely Monodisperse, Highly Repetitive Proteins for Bioconjugates Capillary Electrophoresis: Development and Characterization", Biomacromolecules, vol. 12, pp. 2275-2284 (2011).
Meagher et al., "End-labeled free-solution electrophoresis of DNA", Electrophoresis, vol. 26, No. 2, pp. 331-350 (2005).
Meagher et al., "Free-solution electrophoresis of DNA modified with drag-tags at both ends", Electrophoresis, vol. 27, pp. 1702-1712 (2006).
Meagher et al., "Multiplexed p53 Mutation Detection by Free-Solution Conjugate Microchannel Electrophoresis with Polyamide Drag-Tags", Anal. Chem., vol. 79, pp. 1848-1854 (2007).
Meagher et al., "Sequencing of DNA by free-solution capillary electrophoresis using a genetically engineered protein polymer drag-tag", Anal. Chem., vol. 80, No. 8, pp. 2842-2848 (2008).
Van Hest et al., "Protein-based materials, toward a new level of structural control", Chem. Commun., pp. 1897-1904 (2001).
Vreeland et al., "Molar mass profiling of synthetic polymers by free-solution capillary electrophoresis of DNA-polymer conjugates", Anal., Chem., vol. 73, No. 8, pp. 1795-1803 (2001).
Vreeland et al., "Profiling solid-phase synthesis products by free-solution conjugate capillary electrophoresis", Bioconjugate Chem., vol. 13, No. 3, pp. 663-670 (2002).
Wang et al., "Monodisperse, "highly" positively charged protein polymer drag-tags generated in an intein-mediated purification system used in free-solution electrophoretic separations of DNA", Biomacromolecules, vol. 13, No. 1, pp. 117-123 (2012).
Won et al., "A new cloning method for the preparation of long repetitive polypeptides without a sequence requirement", Macromolecules, vol. 35, pp. 8281-8287 (2002).
Won et al., "Characterization of glutamine deamidation in a long, repetitive protein polymer via bioconjugate capillary electrophoresis", Biomacromolecules, vol. 5, pp. 618-627 (2004).
Won et al., "Protein polymer drag-tags for DNA separations by end-labeled free-solution electrophoresis", Electrophoresis, vol. 26, No. 11, pp. 2138-2148 (2005).

* cited by examiner

*Primary Examiner* — Anand Desai
*Assistant Examiner* — Samuel Liu
(74) *Attorney, Agent, or Firm* — McDermott Will & Emery LLP

(57) ABSTRACT

The present disclosure provides substantially monodisperse random coil polypeptides, vectors encoding the polypeptides, conjugates containing the polypeptides, methods for their preparation, and their uses in nucleic acid separations, DNA sequencing, and other applications requiring high monodispersity.

16 Claims, 14 Drawing Sheets

Gene 1:

ATA TAG AAT TCCTCT TCA↓Gly Ala Gly Thr Gly Ser Ala Gly Ala Gly Thr Gly
         GGT GCG GGC ACC GGA AGT GCA GGT GCT GGA ACG GGC

Ser Ala Gly Ala Gly Thr Gly Ser Ala [SEQ ID NO:32]
AGC GCA GGA GCT GGC ACC GGT TCC GCG↓GGT AGAAGAGGA ATT CAT ATA [SEQ ID NO:29]

FIG. 1A

Gene 2:

ATT CCC C↓TC TAG AAA TAA TTT TGT TTA ACT TTA AGA AGG AGA TAT ACC ATG GCT AGC
                                                        Met Ala Ser

Met Thr Gly Gly Gln Gln Met Gly [SEQ ID NO:33]
ATG ACT GGT GGA CAG CAA ATG↓GGT TGA AGA GCG TAC ATC ATA TGT GCA CGG CTC TTC

↓Gly Ala Ala Ala His His His His His His [SEQ ID NO:34]
A GGT GCG GCC GCA CAT CAT CAT CAT CAT CAC TAA GGA TCC TAA CGC↓TCG AGA TGT C [SEQ ID NO:30]

FIG. 1B

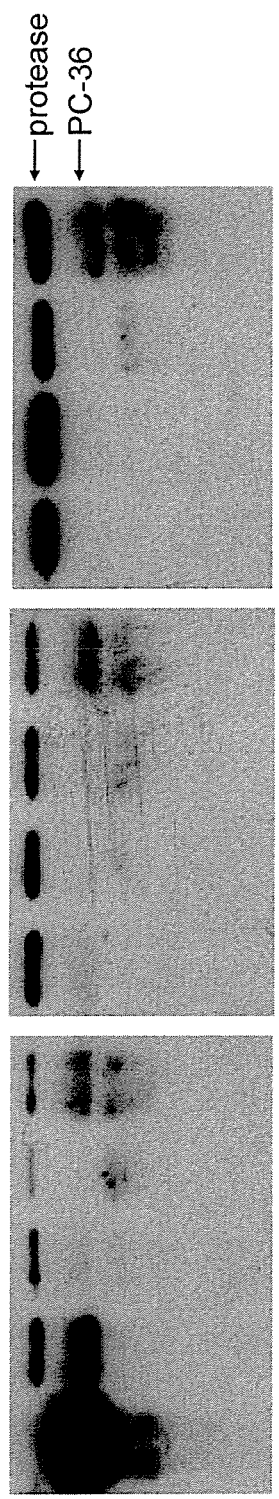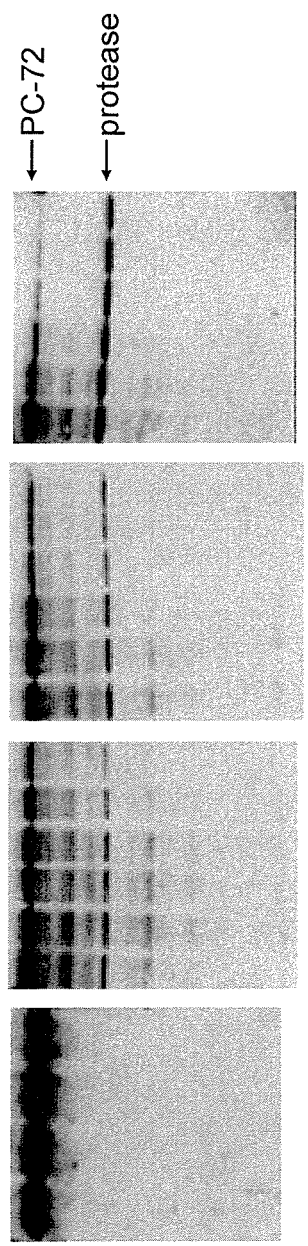
FIG. 5A  FIG. 5B  FIG. 5C  FIG. 5D  FIG. 5E  FIG. 5F  FIG. 5G Gene *R15*:

CTA GCC ATA TGC TCT TCA ↓ GGT ACT GCT GGC TCT GCT GGT GCT GGT TCT GCT GGT Gly Thr Ala Gly Ser Ala Gly Ser Ala Gly

Ser Arg Gly Thr Ala Gly Ser Gly Ala Thr Gly Ala Ser Gly Thr Gly Arg Gly [SEQ ID NO:35]
TCT CGT GGT ACT GCT GGC TCT GGT GCT ACT GGT GCT TCT GGT ACT GGT CGT GGT ↑ TGAAGA GGG

ATC CAC TAG T [SEQ ID NO:31]

FIG. 8

NdeI    SapI                                                              SapI
CATATGGGTTTGAAGAGCCGTACATGAGCTCTGCACGGGCTCTTCAGGTGCCGTGC [SEQ ID NO:26]

FIG. 9

MONODISPERSE RANDOM COIL PROTEINS AND BIOCONJUGATES THEREOF

This application claims the benefit of U.S. Provisional Application No. 61/423,363, filed Dec. 15, 2010, which is herein incorporated by reference in its entirety.

FEDERALLY-SPONSORED RESEARCH OR DEVELOPMENT

This invention was made with Government support under contracts HG002918, HG001970, and CA092752 awarded by the National Institutes of Health. The Government has certain rights in this invention.

REFERENCE TO SEQUENCE LISTING, TABLE OR COMPUTER PROGRAM

A Sequence Listing is submitted with this application in the form of a text file, created Jul. 31, 2014, and titled "0915118269US00seqlist.txt" (16,384 bytes), the contents of which are incorporated herein by reference in their entirety.

TECHNICAL FIELD

The present disclosure relates to substantially monodisperse, water-soluble, random coil proteins and bioconjugates thereof; engineered protein expression vectors genetically encoding these proteins; methods for random coil protein preparation to a high degree of homogeneity of chain length; methods for conjugation of these random coil proteins to other biomolecules; and exemplary uses of DNA-random coil protein conjugates for bioanalyses such as DNA sequencing and other applications that benefit from bioconjugates comprising substantially monodisperse, water-soluble, random coil protein polymers.

BACKGROUND

Proteins substantially comprised of short, repeating amino acid sequence motifs—often called "protein polymers" in the biomaterials literature—can be produced using bacterial protein expression systems, through genetic engineering (e.g., cloning, PCR) and other well-known, widely used techniques of molecular and cellular biology. The *E. Coli*-based expression of long (>250 amino acid) polypeptides comprising highly repetitive, non-naturally derived amino acid sequences, in good yield and with high purity and substantial chain length homogeneity, can be challenging however, especially if the designed proteins have the unusual property of being substantially unstructured ("unfolded") in solution. These particular challenges in achieving high yield and high monodispersity of chain length typically are not so problematic in the *E. Coli*-based expression of well-folded proteins with naturally derived amino acid sequences. In this class of protein-based materials, the repeating amino acid motifs (e.g., Gly-Ala-Gly-Thr-Gly-Ser-Ala; SEQ ID NO: 1) are "macromonomers" that constitute the repetitive protein-based polymer. A chosen amino acid sequence might "mimic" a motif within natural proteins, such as silks or elastins (Prince, et al., *Biochemistry* 1995, 34, 10879-10885; Huang, et al., *Polym. Rev.* 2007, 47, 29-62; Rabotyagova, et al., *Biomacromolecules* 2009, 10, 229-236; Simnick, et al., A., *Polym. Rev.* 2007, 47, 121-154), or instead might be designed "from scratch" (de novo) in the anticipation of fulfilling a particular purpose (Farmer, et al., *Macromolecules* 2006, 39, 162-170; Farmer, et al., *Pharm. Res.* 2008, 25, 700-708). Biosynthetically produced protein polymers are increasingly employed for biomedical applications (e.g., as constituents of tissue engineering scaffolds or as agents enabling the facile purification of other, desired protein targets to which the protein polymers are biosynthetically fused). Such biosynthetic polymers offer certain advantages, if used as an alternative to abiological, synthetic polymers (Davis, et al., *Biomacromolecules* 2009, 10, 1125-1134; Lim, et al., *Biomacromolecules* 2008, 9, 222-230; Petka, et al., *Science* 1998, 281, 389-392; Xu, et al., *Biomacromolecules* 2005, 6, 1739-1749). A polymer that is chemically—as opposed to biosynthetically—produced will inevitably have some degree of polydispersity, i.e., a certain "breadth" in chain length or molar mass distribution, which will depend upon the nature of the chemical reaction used for polymer synthesis. Polydispersity, or chain length inhomogeneity, is non-ideal for certain applications of polymers that have repetitive monomer or macromonomer sequences. This may be the case, in particular, when such polymers are desired for uses in biotechnology or medicine, where purity and homogeneity are often prized and even necessary attributes for proper functioning and characterization.

The properties of protein-based polymers can be customized according to interest by the choice of different DNA sequences to encode the desired amino acid sequence. The only limitations are those of the genetic code (i.e., there are ~20 natural amino acids to choose from), although proteins have been engineered to incorporate certain non-canonical amino acids, and these technologies are becoming increasingly accessible (van Hest, et al., *Chem. Commun.* 2001, 1897-1904; Kiick, et al., *Proc. Natl. Acad. Sci. U.S.A* 2002, 99, 19-24; Connor, et al., *Polym. Rev.* 2007, 47, 9-28; Kim, et al., *J. Am. Chem. Soc.* 2005, 127, 18121-18132). In addition, the chain length of the desired amino acid sequence may, in principle, be specified precisely according to the length of the gene encoding the protein. Protein-based materials produced in biological systems such as the bacterium *E. Coli* can be produced with more precise monomer sequences and more homogeneous chain lengths than conventional, chemically synthesized polymers, which typically are not sequence-specific to the same high degree that proteins are, and which are not completely monodisperse, in the same way that a biosynthesized protein may be (Davis, at al., *Biomacromolecules* 2009, 10, 1125-1134; van Hest, et al., *Chem. Commun.* 2001, 1897-1904; Kiick, K. L., *Polym. Rev.* 2007, 47, 1-7).

Free-Solution Conjugate Electrophoresis (FSCE), which in the past has been called End-Labeled Free-Solution Electrophoresis (ELFSE), uses a pure, substantially monodisperse polymeric tag (sometimes called a "drag-tag", if it fulfills the purpose of adding hydrodynamic drag), tethered end-on to a DNA molecule, to enable size-based separation of a mixture of DNA molecules, by free-solution microchannel electrophoresis. Alternatively, when a particular, monodisperse DNA molecule is attached to a polydisperse preparation of "drag-tags", it is then possible to achieve size-based separation of the drag-tags themselves, and profile their size distribution. It is interesting that FSCE enables the development of substantially novel approaches to DNA sequencing and genotyping, and indeed offers a new method to achieve the size-based separation of DNA for bioanalytical applications. FSCE is better suiting than the more typically used method of gel electrophoresis for DNA separations on microfluidic devices, since FSCE obviates the need for fixed hydrogels or viscous polymer solutions to provide size-based DNA separation. Free-solution operation will save time, reduce cost and complication, and avoid challenges associated with the loading and unloading of the gel or polymer solution ("sieving matrix") in microfabricated electrophoresis devices ("microfluidic chips"). For the purposes of FSCE, an aqueous buffer can be loaded into microchannels using a low applied pressure (e.g., <15 psi) or perhaps by capillary action, which is easy and will facilitate the automation of such microdevices for bioanalytical applications. Free-solution conjugate electrophoresis of DNA or other biomolecules can be more easily implemented in microdevices than any gel-based method, and such devices then could use a wide variety of biomolecule detection schemes, or a wide variety of methods and strategies to assess or control the particular attributes or behavior of a nucleic acid sample or other type of biomolecular sample. Moreover, the types of bioconjugates that are described herein (protein polymer conjugates with nucleic acids) or other conjugates that comprise water-soluble protein polymers with repetitive amino acid sequences, substantially random coil solution conformations, and a high degree of monodispersity could be developed for applications that lie outside of the field of bioanalytical science, for instance, for pharmaceutical or other biomedical or therapeutic uses.

In FSCE, which is primarily aimed at bioanalytical applications, a monodisperse perturbing entity or "drag-tag" with a different molecular charge-to-molecular friction ratio than DNA is attached to nucleic acid polymers. The use of a drag-tag in this manner "breaks" the equivalence of the size-dependence of DNA charge and hydrodynamic friction, the ratio of which dictates electrophoretic mobility. DNA's typical size-independence or its very low degree of size dependence of molecular charge and molecular friction is understood to be a consequence of its unique behavior as a "free-draining coil" during electrophoresis, an attribute that usually prevents its high-resolution, size-based separation in "free solution", i.e., in the absence of a sieving medium such as a porous gel or polymer solution. The presence of a "drag-tag"—i.e., a conjugated molecular modifier that alters the molecular properties and behavior of DNA—has been shown to introduce DNA size-dependence to the electrophoretic mobility of the drag-tag-DNA conjugates, allowing separation in free solution, i.e., in the absence of sieving media of any kind. For example, using a terminal drag-tag as a molecular modifier to single-stranded (ss) DNA molecules produced in the Sanger cycle sequencing reaction, free-solution electrophoretic DNA sequencing can be achieved (Sanger, et al., *Proc. Natl. Acad. Sci. U.S.A.* 1977, 74, 5463-5467), which is a striking achievement because Sanger-based DNA sequencing requires the size-based separation of DNA with single-base DNA chain length resolution. On the other hand, if a drag-tag is not used to modify the Sanger fragments, then the same mixture of ssDNA molecules produced in the Sanger reaction fails to show appreciable DNA size-dependence of electrophoretic mobility; certainly, without a drag-tag, it is impossible to ascertain DNA sequence by free-solution electrophoresis. Recent publications have shown that the larger the hydrodynamic drag provided by the drag-tag (i.e., generally, the larger the size of the drag-tag), the greater the length of the DNA sequencing fragments that can be resolved, and consequently, the longer the "read length" (zone of contiguous DNA base sequences ascertained) that can be obtained by FSCE. In addition to higher drag, longer read lengths are obtained if the drag-tag preparation used for DNA modification is substantially monodisperse in its molecular size, molecular structure, and chain length if the drag-tag is a polymer.

Indeed, an advantageous drag-tag for use in FSCE will be completely or substantially monodisperse, easily water-soluble, uncharged or possessing a low degree of positive electrostatic charge, and will show minimal adsorption to or non-specific interaction with the glass (fused silica) microchannel walls. Additionally, to be useful for FSCE, a drag-tag must be able to be uniquely and stably attached to DNA, preferably "end-on", i.e., at one of the DNA's molecular termini (Meagher, et al., *Anal. Chem.* 2008, 80, 2842-2848). From this imposing list of needed attributes for an advantageous FSCE drag-tag, perhaps the most important property for a drag-tag is complete monodispersity, such that each and every drag-tag molecule in a preparation that is conjugated to DNA molecules is identical in its chain length, amino acid sequence, and particular chemical structure, and hence, is identical in its net, counterion-screened electrostatic charge and the hydrodynamic drag it generates in free-solution electrophoresis. If a polydisperse preparation of molecules is used as drag-tags for FSCE-based DNA analysis, the resulting bioconjugates are similarly polydisperse, and this has deleterious effects on the usefulness of the data obtained in the bioanalytical separation. In this case, the peak pattern obtained by microchannel electrophoresis would be complex, because for any given DNA molecule in the nucleic acid mixture of interest, i.e., for DNA of any particular chain length, there will be multiple peaks in the electropherogram, instead of a single peak, as is most desirable and useful for bioanalytical applications. The DNA drag-tag conjugate peaks for a particular DNA molecule may overlap with peaks corresponding to bioconjugate peaks for DNA molecules of different sizes—this would certainly be the case for a DNA sequencing sample prepared by the Sanger reaction—which would make accurate DNA sizing difficult or impossible. This requirement for total monodispersity eliminates from consideration all of the commonly available chemically synthesized polymers, microparticles, and nanoparticles, and makes such polymers or particles poor candidates for FSCE DNA sequencing drag-tags; none of these is completely and totally monodisperse (Meagher, et al., *Electrophoresis* 2005, 26, 331-350). Although solid-phase synthesis techniques can be used to generate monodisperse, sequence-specific polyamide molecules such as polypeptides and polypeptoids (i.e., poly-N-substituted glycines), solid-phase synthesis technology produces polyamides that are too small/too short in chain length to generate sufficient hydrodynamic drag for the separation of large ssDNA fragments (>120 bases in length) for FSCE sequencing (Haynes, et al., *Bioconjugate Chem.* 2005, 16, 929-938).

Natural proteins are very often much larger in size than polyamides produced by solid-phase synthetic approaches, however, natural proteins have other drawbacks that make them unsuitable as drag-tags for bioanalytical applications. For instance, in aqueous solution, most natural proteins are "folded" into compact, three-dimensional chain configurations ("conformations"), and typically present numerous positive and negative surface charges. Charged proteins could have deleterious electrostatic interactions with the DNA analytes, or with the glass microchannel walls of the electrophoresis chamber. For instance, proteins with a high density of positive charges could ionically bind to DNA molecules, or to the microchannel wall, or both. But on the other hand, proteins with a high degree of negative charge will tend to electrophorese in the same direction as the DNA molecules themselves, and so might not substantially change the size-dependence of electrophoretic mobility. This is why a DNA modifier that is close to net-neutral in its charge will be most desirable for FSCE, if one is able to identify a substantially uncharged modifier which is also water-soluble and which also allows facile end-on attachment to DNA molecules. It should also be considered that natural proteins typically contain a variety of different chemically reactive groups as amino acid "side chains" (e.g., a primary amine group in lysine, a thiol in cysteine, a carboxylic acid in both glutamic acid and aspartic acid). The presence of these chemically reactive groups in a protein can make the unique, precise, chemoselective attachment of natural proteins to DNA molecules, through a very particular site on the protein, difficult if not impossible. In contrast, properly designed and properly prepared, sequence-engineered protein polymers are able to meet the many stringent requirements of a useful drag-tag, through careful design of the repetitive amino acid "macromonomer" sequence, in such a way as to reduce or eliminate the number of potentially problematic charged and reactive sites. As discussed previously, biosynthetically produced protein polymers also can, in principle, be produced with a much higher degree of homogeneity of their physical structure and molecular properties than chemically synthesized polymers.

As mentioned above, FSCE itself also can be used as a highly sensitive, fluorescence-based detection method to investigate the polydispersity of a given preparation of a protein polymer drag-tag, and this method is very important, in fact, for the assessment of the purity and homogeneity of a candidate drag-tag preparation for DNA sequencing applications. To accomplish this, a preparation of potential protein drag-tags is conjugated end-on to a monodisperse, fluorescently labeled oligonucleotide primer, and the obtained bioconjugates are analyzed by free-solution microchannel electrophoresis. If one is characterizing a candidate drag-tag preparation, it is preferable to observe only two peaks in this type of electropherogram: (1) a peak representing free (un-conjugated) DNA, which passes the detector first given the absence of a "drag-tag", followed by a peak representing drag-tag-DNA conjugates, eluting later because DNA's electromigration velocity is reduced as a result of the added hydrodynamic drag associated with the attached drag-tag molecule, which it "pulls" along with it as it moves in an applied electric field. This method also has been used to characterize a the breadth of chain length distribution in a commercially obtained preparation of "monodisperse" (PDI or Polydispersity Index=1.01, considered herein to be very low) synthetic polyethylene glycol) (PEG), to which a monodisperse, fluorescently labeled DNA molecule was conjugated end-on via chemical methods (Vreeland, et al., Anal. Chem. 2001, 73, 1795-1803). An analysis by capillary electrophoresis revealed more than 110 different bioconjugate peaks, which were well-resolved from each other, in an overall Gaussian distribution of PEG-DNA bioconjugates comprising PEGs of differing chain lengths. It was striking, in this example, that single-monomer differences in PEG structure, i.e., different numbers of —$CH_2CH_2O$— units, and even the difference of one such monomer unit, were enough to produce distinct peaks that were resolvable by FSCE, demonstrating the tremendous resolving power as well as the high sensitivity of this technique to provide useful electrophoretic mobility shifts for a sample of interest, based on small molecular differences. FSCE has also been used to characterize solid-phase polypeptoid synthesis products (Vreeland, et al., Bioconjugate Chem. 2002, 13, 663-670) and to assess and analytically profile the deamidation (chemical degradation) products of a family of protein polymers comprising a significant number of glutamine residues (because glutamine can become converted to glutamic acid residues, over time, via undesired chemical reactions in water) (Won, et al., Biomacromolecules 2004, 5, 1624-1624).

The design, purification, and obtainment of sufficient, useful amounts of completely or substantially monodisperse protein polymers, which are suitable as drag-tags for FSCE-based DNA sequencing, was a challenging task requiring more than 12 years of steady molecular engineering work. The first family of reported protein polymer drag-tag designs of various lengths and amino acid sequences were found to be heterogeneous after purification from bacterial cultures, when assessed by FSCE using a monodisperse, fluorescently labeled oligonucleotide, despite the fact that these protein polymers had been produced in a simple biological system, E. coli, according to what was understood to be the most commonly used, methods for heterologous protein expression in bacteria (Meagher, et al., Electrophoresis 2005, 26, 331-350; Won, et al., Biomacromolecules 2004, 5, 1624-1624; Won, et al., Electrophoresis 2005, 26, 2138-2148). However, recently, a small, random coil, substantially monodisperse protein polymer drag-tag comprising 127 amino acids was produced and tested as a FSCE drag-tag. This 127mer protein polymer was demonstrated to be useful for "short-read" Sanger DNA sequencing in free solution, providing a reproducibly obtainable read length of ~180 bases of contiguous DNA sequence (Meagher, et al., Anal. Chem. 2008, 80, 2842-2848). To obtain longer read lengths (>400 bases) by FSCE (as would be desired because a typical human exon, in an expressed gene, is at least 400 bases long), our originally developed methods and strategies for the preparation of biosynthetic polypeptide drag-tags were found to be insufficient to produce polypeptides with substantial and bioanalytically sufficient levels of monodispersity.

BRIEF DESCRIPTION OF THE DRAWINGS

FIG. 1A depicts the DNA sequence of the macromonomer that was used initially to generate the repetitive genes of Example 1. EarI restriction sites are in bold and underlined, and arrows indicate the cleavage site of the enzyme.

FIG. 1B depicts the 179-bp DNA sequence used to replace the existing cloning region of a commercially obtained pET-41a plasmid. In the sequence, the SapI restrictions sites are shown with double underlining, while XbaI and XhoI sites are underlined once.

FIG. 5 depicts the results of a Western blot analysis of the protein products of an endoproteinase GluC proteolytic digestion of the protein preparation code-named "PC-36", over the course of 16 hours: (A) PC-36, with no added protease; 2, 4, 8, and 16 hours after 1:100 μg protease:μg protein was added, for: (B) 2, 4, 8, and 16 hours after 1:50 μg protease:μg protein was added; (C) 2, 4, 8, and 16 hours after 1:20 μg protease:μg protein was added. Additionally, the figure shows the results of Western blot analysis performed after the endoproteinase GluC digestion of the "PC-72" protein preparation over 12 hours: (D) PC-72 incubated in digestion buffer for 0, 4, 8, and 12 hours, but with no protease added; and (E) 2, 4, 6, 8, 10, and 12 hours after adding 1:100 μg protease:μg protein; and (F) 2, 4, 6, 8, 10, and 12 hours after the addition of 1:50 μg protease:μg protein, and (G) 2, 4, 6, 8, 10, and 12 hours after the addition of 1:20 μg protease:μg protein.

FIG. 8 depicts the 113-bp DNA sequence using in the cloning process, to produce a novel gene sequence for the production of the desired protein polymer. EarI restriction sites are shown in bold text and underlined, and arrows indicate the cleavage site of the enzyme.

FIG. 9 depicts the 54-bp DNA sequence used to replace the existing cloning region of the pTXB1 cloning plasmid. In the sequence, two SapI restrictions sites are shown in bold text. The NdeI restriction site is underlined.

DETAILED DESCRIPTION

Definitions

Figure 2:
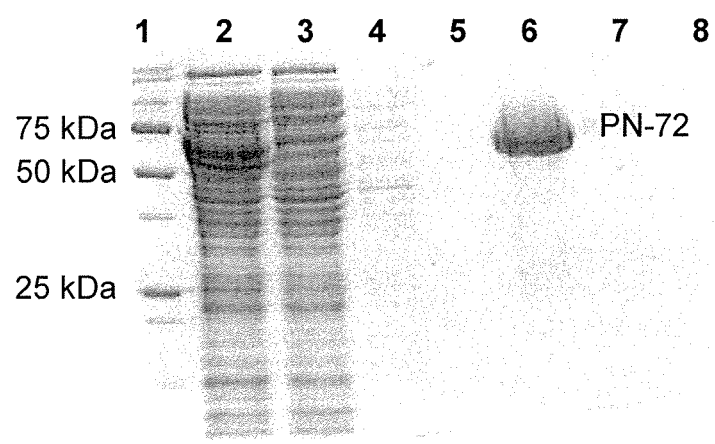
FIG. 2 depicts the results of electrophoresis using a 12% SDS-PAGE gel for the analysis of a protein preparation that was code-named "PN-72", which had been purified from E. coli cell lysate using immobilized metal affinity chromatography (IMAC) on a column containing Talon® cobalt-chelated resin. Lane 1: protein standards; Lane 2: clarified cell lysate; Lane 3: column flow-through; Lanes 4-5: washes; lanes 6-8: different eluted protein fractions.

It is to be understood that this disclosure is not limited to the particular embodiments described, as such may vary. It is also to be understood that the terminology used herein is for the purpose of describing particular embodiments only, and is not intended to be limiting, as the scope of the present invention will be limited only by the appended claims.

All publications mentioned herein are incorporated herein by reference to disclose and describe the methods and/or materials in connection with which the publications are cited. It is understood that the present disclosure supersedes any disclosure of an incorporated publication to the extent there is a contradiction.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

As used herein, the following definitions shall apply unless otherwise indicated.

As used in this specification and the appended claims, the singular forms "a", "an" and "the" include plural referents unless the context clearly indicates otherwise. Thus, for example, reference to "a protein" includes more than one protein, and reference to "a compound" can refer to more than one compound. In describing and claiming the present invention, the following terminology will be used in accordance with the definitions set out below.

When the three-letter abbreviations are used, unless specifically preceded by an "L" or a "D" or clear from the context in which the abbreviation is used, the amino acid may be in either the L- or D-configuration about α-carbon ($C_\alpha$). For example, whereas "Ala" designates alanine without specifying the configuration about the α-carbon, "D-Ala" and "L-Ala" designate D-alanine and L-alanine, respectively.

When peptide sequences are presented as a string of one-letter or three-letter abbreviations (or mixtures thereof), the sequences are presented in the N→C direction in accordance with common convention.

The term "random coil polypeptide" refers to a linear chain of amino acids, based on a polyamide backbone identical to that of natural proteins, which do not adopt any non-random secondary structures or local "folds", such as α-helices or β-sheets.

The term "random coil polypeptide conjugates" refers to conjugates that comprise the random coil polypeptide and one or more molecules such as those from the group consisting of a nucleic acid, an oligopeptide, a polypeptide, a heterobifunctional chemical cross-linker, a synthetic polymer, and a chemically synthesized polyamide or other water-soluble polymer.

The term "affinity tag" refers to an amino acid sequence that is capable of binding to an immobilizable substrate, thereby facilitating the isolation of polypeptides containing this tag from any non-tagged impurities. The term "C-terminal affinity tag" or "traces thereof" refers to affinity tags appended at the carboxy terminus or "C" terminus of the polypeptide and to any residual amino acid sequences of the C-terminal tag that remain following a particular tag removal or cleavage procedure. In some aspects, "traces of the C-terminal affinity tag" refers to residual amino acids left after cleavage of the tag by a protease such as those selected from the group consisting of enterokinase, thrombin, Factor Xa, tobacco etch virus (TEV), and endoproteinase GluC.

The term "affinity column" refers to a column containing the immobilizable substrate. For example, affinity columns for polyhistidine-tagged polypeptides may contain transition metal resins that bind to the histidine tag, such as a Ni(II)-nitrilo-triacetic acid (Ni-NTA) resin or a Cobalt-based resin. Purification of the polyhistidine-tagged polypeptides on such a column allows for the use of mild conditions and/or a range of denaturing conditions, for the obtainment of substantially pure protein preparations.

The term "polyhistidine tag" refers to tags containing multiple histidines, such as a hexahistidine tag (His-tag) or a octa- or decahistidine amino acid sequence "tag".

The term "nucleic acid fragment" refers to nucleic acids such as those generated in a Sanger sequencing method or cycle sequencing method (the latter involving the use of Polymerase Chain Reaction amplification of DNA), and includes DNA (deoxyribose nucleic acid) nucleotides and variants such as chain-terminating dideoxynucleotides. In some aspects the nucleic acid fragment is an oligonucleotide DNA sequencing primer.

The term "completely monodisperse" refers to polypeptides that are 100% identical in charge and drag. The term "substantially monodisperse" refers to polypeptides having at least 92% or at least 95% amino acid sequence identity. In some aspects, substantially monodisperse polypeptides have at least 98% or at least 99% identity. Monodispersity and polydispersity can be measured by free-solution conjugate electrophoresis (FSCE) with monodisperse, fluorescently labeled DNA primers, a technique that does not require a gel or a sieving matrix for separation. In the standard theory of FSCE (C. Desruisseaux, D. Long, G. Drouin, G. W. Slater, *Macromolecules* (2001) vol. 34, p. 44; L. C. McCormick et al., Journal of Chromatography A (2001) vol. 924, p. 43; R. J. Meagher et al., *Electrophoresis* (2006) vol. 26, p. 331), the electrophoretic mobility of a composite object is determined by a weighted average of the electrophoretic mobilities of charged DNA and uncharged drag-tag monomers. Mathematically, this weighted average mobility for a chain with $M_c$ charged DNA monomers and $M_u$ uncharged monomers is:

$$\mu = \mu_0 \frac{M_c}{M_c + \alpha_1 M_u}$$

wherein $\mu_0$ is the free-solution electrophoretic mobility of DNA (independent of size), and $\alpha_1$ is a weighting factor that rescales the number of uncharged monomers based on differences in size and persistence length as compared to the DNA monomers. Uncharged polymer chains are considerably more flexible than ssDNA, and typical values of $\alpha_1$ range from ⅕ to ⅙. Accordingly, the product $\alpha = \alpha_1 M_u$ has frequently been used to characterize the overall drag provided by a drag-tag, and can be calculated from experimental data.

The term "polypeptide drag-tag" refers to synthetic, substantially uncharged or moderately positively charged polypeptides (with formal electrostatic charges <+18) having repeating amino acid sequences, for use in Free-Solution Conjugate Electrophoresis or for another purpose. In one embodiment, the polypeptide drag-tag modifies the electrophoretic mobility of nucleic acid chains. The polypeptide drag-tag is preferably water-soluble at room temperature in a buffer with pH between 5 and 9, in the absence of added denaturants such as urea or guanidinium chloride salts, and remains substantially "unfolded", i.e., in a substantially random coil chain configuration. In some aspects, the polypeptide drag-tag may or may not comprise a C-terminal affinity tag or the remnants thereof that remain after a process aimed at substantially removing the C-terminal affinity tag. In other aspects, the polypeptide drag-tag is capable of providing the free-solution electrophoretic separation, identification, or inferred molecular characterization of nucleic acid fragments that are at least 150, 180, 200, 250, 300, 350, 400, 500, 600, 700, 800, 900, or 1000 nucleotide bases in length.

C-terminal affinity tags are not commonly used for the purification of proteins expressed in *E. Coli*, since proteases typically cleave C-terminal to the protease binding site of the tagged protein, so that any C-terminal affinity tag will fail to be "excised" or removed completely, meaning that typically, traces of any C-terminal affinity tag will be left behind on the protein. Strikingly and after much work aimed at reducing polydispersity of preparations of random coil protein polymers expressed in *E. Coli*, the inventors have now found that polypeptides prepared from precursors expressed with a C-terminal tag have much greater degrees of monodispersity, in comparison to random coil protein polymers that are prepared using amino-terminal or N-terminal affinity tags. Moreover, C-terminal tags has been found to allow the purification of substantially full-length, expressed random coil polypeptides from the *E. Coli* cell lysate, as only completely expressed polypeptides possess the full affinity tag on their C-termini. Hence, the use of a C-terminal affinity tag is strictly necessary to prevent the co-elution of incompletely translated proteins, which for whatever reason unique to the biological processes within the *E. Coli* cells, were not produced at the full, intended chain length comprising a highly repetitive amino acid sequence.

Accordingly, in one embodiment, provided is a method for preparing a substantially monodisperse, random coil polypeptide the method comprising: a) providing a DNA plasmid expression vector encoding a random coil polypeptide that comprise a C-terminal affinity tag; b) expressing the polypeptide; and c) contacting the expressed polypeptide with an affinity column that has an affinity for the incorporated C-terminal tag.

In some embodiments, the affinity tag is a polyhistidine or a T7 tag.

In some embodiments, the affinity column comprises a nickel or cobalt resin.

"Intein" refers to a naturally occurring or artificially-created polypeptide or protein splicing element that mediates its excision from a precursor polypeptide or protein and the joining of the flanking polypeptide or protein sequences ("exteins"). A list of known inteins is available on the worldwide web at .neb.com/inteins.html; polynucleotides encoding such inteins are available on the worldwide web atneb.com/inteins/int-reg.html. Unless specifically noted otherwise, an intein may be a "contiguous intein" which is composed of a single polypeptide chain or a "split intein" which is composed of two or more distinct polypeptide chains.

In some embodiments, the affinity tag comprises an "intein" domain, which can "self-cleave" or essentially remove itself under certain solution conditions. Suitable intein domains include those that are commercially available from, for instance, New England Biolabs, Inc. In some aspects, the affinity tag comprises both an intein and a chitin-binding domain. In some such aspects, the affinity column used comprises chitin.

In some embodiments, the method further comprises exposing the expressed polypeptide to one or more of a protein cleaving reagent that cleaves only at a particular amino acid sequence, a change in pH, or a change in temperature to remove the affinity tag.

In some embodiments, the cleaving reagent is a protease selected from the group consisting of enterokinase, thrombin, Factor Xa, tobacco etch virus (TEV), and endoproteinase GluC. In some aspects the cleaving reagent is enterokinase.

In some embodiments, the cleaving reagent is dithiothreitol (DTT), which can induce the intein domain's self-cleavage.

In some embodiments, the polypeptide is expressed in a BLR(DE3) E. coli cell. This cell has its recombinase gene (recA) knocked out, compared to the more commonly utilized BL21 strain, which is important because the lack of recA reduces the incidence of random gene recombination events, which can lengthen or shorten the gene, and contribute to heterogeneity of the final expressed protein.

In some embodiments, the method further comprises purifying by reversed-phase high performance-liquid chromatography (RP-HPLC) or fast performance liquid chromatography (FPLC) the polypeptide preparation, with or without its affinity tag attached. Such purifications have been found herewith to aid in removing impurities such as endotoxins (lipolysaccharides from bacterial cell walls), which otherwise might remain associated with bacterially expressed proteins even through a standard affinity purification procedure.

In one embodiment, provided is a vector encoding a substantially monodisperse random coil polypeptide comprising a C-terminal affinity tag. In some embodiments the vector is aMpET41a vector encoding the polypeptide with an N-terminal T7 tag and C-terminal His tag.

In some embodiments the vector is a MpTXB1 vector encoding a substantially monodisperse random coil polypeptide with a C-terminal intein-CBD tag.

In one embodiment, provided is a substantially monodisperse random coil polypeptide comprising a C-terminal affinity tag or traces thereof.

In one embodiment, provided is a conjugate comprising a substantially monodisperse random coil polypeptide having a C-terminal affinity tag or traces thereof and one or more molecules selected from the group consisting of a nucleic acid, an oligopeptide, a polypeptide, a heterobifunctional chemical cross-linker, a synthetic polymer, a polyamide, and a water soluble polymer. In some aspects, the heterobifunctional cross-linker or synthetic polymer comprises oligoethylene glycols or polyethylene glycols.

In one embodiment, provided is a conjugate comprising a substantially monodisperse random coil polypeptide drag tag having a C-terminal affinity tag, wherein the polypeptide drag tag is attached to a linker that is attached to a nucleic acid fragment. In one embodiment, the polypeptide drag tag is attached at its N terminus to the linker. In some aspects the nucleic acid fragment is a DNA sequencing primer. In some aspects, the linker is sulfo-SMCC.

In one embodiment, provided is a kit comprising one or more of a vector, a polypeptide, or a conjugate as disclosed herein. In some embodiments, the kit further comprises reagents such as one or more of a polymerase, buffer, primer, and instructions for their use. In other embodiments, the kit further comprises one or more dideoxy nucleotides.

In one embodiment, provided is a method of sequencing comprising the use of one or more of a vector, a polypeptide or a conjugate as disclosed herein. In some embodiments, the method of sequencing comprises determining the presence or absence of a single nucleotide polymorphism (SNP).

The aforementioned embodiments may have one or more of the following features.

In some embodiments, the random coil polypeptide, having or prepared from a non-intein-containing C-terminal tag, is greater than 250 amino acids in length. In other embodiments the polypeptide is at least 300, 350, 400, 450, 500, or 550 amino acids in length.

In other embodiments, the polypeptide is less than 250 amino acids in length. In some aspects the polypeptide is between 90 and 120 amino acids in length.

In some embodiments, the polypeptide has at least 10 amino acid repeats, each composed of at least five amino acids. In other embodiments, the polypeptide has at least 10 amino acid repeats of at least seven amino acids. In still other embodiments, the polypeptide has at least 30 to 70 amino acid repeats of a sequence of at least seven amino acids.

In some embodiments, the polypeptide has at least one or a first amino acid sequence that repeats, wherein the amino acids of the sequence are independently selected from glycine, alanine, threonine, serine, and arginine. In other embodiments the methods, vectors, or polypeptides as described herein further comprise a second repeating amino sequence wherein the first and second sequences are not identical, which comprises a sort of "block co-polypeptide".

In some embodiments, the polypeptide comprises on average evenly spaced arginines. In some embodiments, the arginines on average are spaced every 18 amino acids.

In some embodiments, the polypeptide comprises a repeating amino acid sequence selected from one or more of GAGTGSA (SEQ ID NO: 1) and GAGTGRA (SEQ ID NO: 2), using the one-letter code for the amino acids. In other embodiments, one, two, or three amino acids of the repeating sequence is substituted with a different amino acid. In still other embodiments, the different amino acid is not lysine.

In some embodiments, the repeats are joined end-to-end or are separated by spacers, including additional amino acid sequences.

In some embodiments, the polypeptide comprises conserved or non-conserved amino acid substitutions at one or more (e.g., 2, 3, 4, . . . etc.) positions in each repeating unit or one or more positions in a subset of the repeating units in the polymer. In some embodiments, at least 60% (e.g., 65%, 75%, 80%, 90%, 95%, etc.) of the amino acids in the polypeptide are not substituted. For example, as used herein Gly (glycine), Ala (alanine), Ser (serine) and Thr (threonine) are known as relatively polar or hydrophilic, uncharged amino acids, as are Asn (asparagine), Trp (tryptophan), and Gln (glutamine). A plurality of these amino acids, with the greatest number of amino acids being chosen from among Gly, Ala, Ser, and Thr, can be chosen to create a protein that is water-soluble and that will tend to have a predominantly unfolded (random coil) structure in aqueous solution. In some embodiments, sparing use can be made of negatively charged amino acids such as Asp (aspartate), and Glu (glutamate) to increase water-solubility. Further, Leucine (Leu) is a relatively hydrophobic amino acid as are Phe (phenylalanine), Ile (isoleucine), Pro (proline) and Val (valine). It is contemplated that these amino acids can be used, but more sparingly than the relatively hydrophilic amino acids defined above. In some embodiments, certain sulfur-containing amino acids such as Cys (cysteine) and Met (methionine) can be used in very small amounts if at all, since they are highly chemically reactive (Voet and Voet, Biochemistry, 2nd Ed., John Wiley & Sons, Inc. pp. 1361). Additional functionally equivalent properties of amino acids are described, for example, in Taylor, J. Theor. Biol. (1986) 119(2):205-18 (incorporated herein in its entirety), where a Venn diagram of the relationship between the 20 amino acids is depicted using the parameters of size, aliphatic and aromatic properties, hydrophobicity, charge and polarity. It is contemplated that any of the amino acids demonstrating similar functional properties are interchangeable in generating a polymer of the present invention.

In some embodiments, the polypeptide comprises a protease recognition sequence at its C-terminal end.

In some embodiments, the polypeptide comprises a recognition sequence for enterokinase, thrombin, Factor Xa, tobacco etch virus (TEV), or endoproteinase GluC. In some embodiments, the recognition sequence is E for binding to GluC. In some embodiments, the recognition sequence is IEGR (SEQ ID NO: 22) for binding to Factor Xa or GluC.

In some embodiments, the polypeptide comprises a T7 tag at the N-terminus. In other embodiments, the T7 tag comprises the sequence, MASMTGGQQMG (SEQ ID NO: 3). In some embodiments the polypeptide further comprises repeating sequences GAGTGSA (SEQ ID NO: 1) and GAGTGRA (SEQ ID NO: 2) with a IEGR sequence (SEQ ID NO: 22) at the C-terminus. In other embodiments, a polyhistidine sequence such as His$_8$ is attached to the arginine amino acid of the IEGR (SEQ ID NO: 22) sequence. In some aspects the polypeptide comprises the repeating sequence GAGTGSA (SEQ ID NO: 1) with 27, 36, 54, or 72 repeating units where one in every nine repeating units contain arginine in place of serine.

In one embodiment the polypeptide comprises repeating sequence GAGTGSA (SEQ ID NO: 1) with 36 repeating units where one in every nine repeating units contains arginine in place of serine.

The random coil polypeptides as disclosed herein can be covalently attached to nucleic acid fragments or other molecules via linkers such as heterobifunctional linkers. Heterobifunctional linkers include sulfo-SMCC linker having the chemical structure:

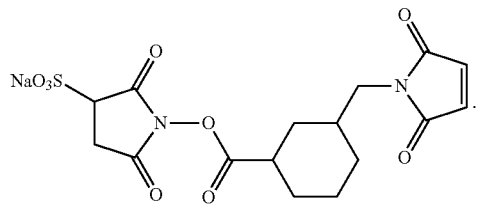

The sulfo-SMCC can link the N-terminal end of the random coil polypeptide to a thiol-terminated DNA sequence to give the following protein-linker-DNA conjugate:

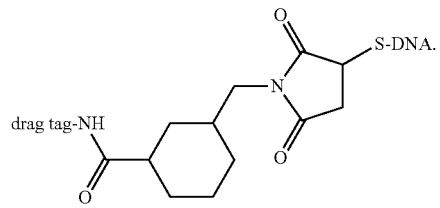

In some embodiments, the polypeptides as provided herein are purified under native conditions to prevent unintended reactions that can lead to polydispersity. In some embodiments protease inhibitors are added during the purification to reduce possible native E. coli. protease activity.

Use of urea (denaturing conditions) can result in potential carbamylation of the N-terminus and also of any lysine and arginine side chains that may be present. In some embodiments when denaturing conditions are used, the polypeptide is purified using guanidine hydrochloride as a denaturant. In other embodiments, fresh urea buffers are used.

In some embodiments, the random coil polypeptides provided herein are for use as drag-tags in nucleic acid separations and sequencing. Applications include separations in free-solution such as by free-solution microchannel electrophoresis in devices such as microfluidic chips. In some embodiments, the separations are conducted in free solution in capillary tubes.

In some embodiments, provided is a method for determining the monodispersity of a polypeptide by use of free-solution conjugate electrophoresis (FSCE). FSCE can provide better resolution than MALDI-TOF in identifying mass differences in large (>20 kDa) protein polymers that often are seen as a single, broad peak by mass spectrometry. Chromatographic methods such as RP-HPLC are also unable to distinguish between different lengths of the same protein polymer sequence which elute at nearly identical acetonitrile concentrations in water, regardless of significant differences in chain length. FSCE is also sensitive to charge differences between nearly identical protein polymers and not just mass, thereby allowing for determination of the true monodispersity of a protein polymer, better than that afforded by standard methods.

In some embodiments, the random coil polypeptides and conjugates thereof as provided herein are for use in detection of single nucleotide polymorphisms (SNP) to facilitate detection and diagnosis of disease states such as, for example, cancers, cystic fibrosis, muscular dystrophy, Alzheimer's disease, diabetes, and sickle cell anemia. In some embodiments, the polypeptides are used to detect a subject with a genetic predisposition to a disease state. In some embodiments, the polypeptides are used to analyze a subject's SNP profile for predicted drug therapy efficacy and potential design of useful therapeutics for a particular individual based on the SNP profile (e.g., for personalized medical treatments).

In other embodiments, the random coil polypeptides and conjugates thereof are used in other, non-FSCE applications where a water-soluble, random coil polypeptide with very high or substantial monodispersity is required. Such applications can include use in therapeutic agents, such as biomolecules comprising polymer modifications such as a polyethylene glycol modifier, where a random coil, water-soluble polypeptide expressed by the methods taught herein can be used in the place of polyethylene glycol, to perform substantially similar functions.

Using the compositions and methods of the present disclosure, the longest sequencing read ever recorded by FSCE separations was achieved, and longer drag-tags are expected to give even longer reads. The protein polymer drag-tags were incorporated into the traditional Sanger reaction with ease, providing a notable advantage. The primers were conjugated to the drag-tags and included in the reaction without modification to the standard cycling protocol. While previous studies used the SNaPshot™ kit, this study used the BigDye™ kit (both ABI), demonstrating that the method is kit-independent (Meagher, et al., *Anal. Chem.* 2008, 80, 2842-2848). Both yield sequencing peaks with no sign of degradation from the presence of the drag-tag.

The following examples are provided to illustrate certain aspects of the present methods, compositions, and systems and to aid those of skill in the art in practicing the described subject matter. These examples are not to be considered to limit the scope of the disclosed subject matter.

EXAMPLES

All molecular biology techniques were conducted according to standard protocols or from instructions provided by manufacturers unless otherwise noted. Unless specifically stated, all enzymes were obtained from New England Biolabs (NEB, Ipswich, Mass.). The intein-mediated purification system (including the unmodified pTXB1 vector and chitin beads) was also purchased from NEB. General reagents for cloning and protein expression were obtained from Fisher Scientific (Pittsburgh, Pa.) unless noted otherwise.

Example 1

A. Creation of Multimer Gene

A 102-bp single-stranded synthetic oligonucleotide was designed to consist of three repeats of the seven amino acid sequence Gly-Ala-Gly-Thr-Gly-Ser-Ala (SEQ ID NO: 1). The gene sequence is shown in FIG. 1A. The oligonucleotide was purchased from Integrated DNA Technologies (IDT, Coralville, Iowa) and was PCR-amplified using high fidelity Pfu DNA polymerase (Stratagene, La Jolla, Calif.). The PCR product was then digested at 37° C. by EarI. The fully cleaved 63-bp fragment was isolated and purified from undigested products by agarose gel electrophoresis and the QIAEX II Gel Extraction Kit (Qiagen, Valencia, Calif.). Multimers of the gene were generated by self-ligation using T4 DNA ligase. These multimers were inserted into a modified pUC18 cloning vector containing flanking SapI sites in accordance with the controlled cloning method previously disclosed for generating larger genes from multimers without sequence requirements based on the use of two Type IIS endonucleases, SapI and EarI (Won, et al., *Macromolecules* 2002, 35, 8281-8287). These restriction enzymes cut downstream of their recognition sites. Note that circularization of sufficiently long DNA multimers limits the size of the multimer gene that can be obtained simply by self-ligation. The plasmids were transformed via heat shock into NovaBlue competent cells (Novagen, Madison, Wis.). The resulting transformants were screened by DNA sequencing to verify the identity and size of the insert DNA. Sequencing showed that the selected multimer gene, consisting of 18 repeats of the 7 amino acid sequence, had two serine to arginine mutations and that the actual sequence was (GAGTGSA)$_4$GAGTGRA (GAGTGSA)$_7$GAGTGRA(GAGTGSA)$_5$ (herein identified as SEQ ID NO: 4). This sequence was designed to be random coil in structure (Garnier, et al., *Methods Enzymol.* 1996, 266, 540-553), providing greater hydrodynamic drag than a similarly sized but more compact, globular protein. A small number of positively charged residues are actually beneficial to FSCE separations as the charges "pull" the drag-tag in the opposite direction of the negatively charged DNA in an electric field, effectively increasing the hydrodynamic drag (Coyne, et al., In *Handbook of Capillary and Microchip Electrophoresis and Associated Microtechniques*, 3rd ed.; Landers, J. P., Ed. CRC Press: New York, 2008; p 1567). The gene encoding 18 repeats of the 7 amino acid sequence (with mutations) was doubled twice by controlled cloning to produce genes 36 and 72 repeats long. Note that EarI is an analog of Eam1104 I and either enzyme can be used in conjunction with SapI for this cloning strategy.

B. Generation of Expression Vector with C-Terminal Affinity Tag

Site-directed mutagenesis (QuikChange Kit, Stratagene, La Jolla, Calif.) was used to alter the two existing SapI sites of pET-41a (Novagen) into EarI recognition sites. Primer sequences 5'-CTT GAA GAA AAA TAT GAG GAG CAT TTG TAT GAG CGC GAT G-3' (SEQ ID NO: 5) and 5'-GAG GAA GCG GAA GAG AGC CTG ATG CGG-3' (SEQ ID NO: 6) along with their respective reverse complementary sequences (four primers total) were designed according to the manufacturer's guidelines and purchased as PAGE-purified DNA oligomers from IDT. Two rounds of mutagenesis were performed according to the suggested manufacturer's protocol. SapI digestion of the recovered plasmid DNA confirmed the modifications were successful based on the observation of intact vector on an agarose gel.

Assembly PCR was used to generate a 179-bp oligonucleotide (FIG. 1B), containing a T7 tag (MASMTGGQQMG; (SEQ ID NO: 3) for enhanced expression and an octahistidine tag for affinity purification, to be inserted into the multiple cloning site of the expression plasmid. Six synthetic oligonucleotides were designed with overlapping bases and similar melting temperatures (55° C.) according to the outlined protocol for assembly PCR (Rydzanicz, et al., *Nucl. Acids Res.* 2005, 33, W521-525) along with flanking primers. The oligonucleotides used to generate the 179-bp fragment by assembly PCR are listed below (presented in the 5'→3' direction in accordance with common convention).

| | Sequence | SEQ ID NO: |
|---|---|---|
| Oligo 1 | ATTCCCCTCTAGAAATAATTTTGTTTAACTTTAAGAAGGAGATATACC | 7 |
| Oligo 2 | CACCAGTCATGCTAGCCATGGTATATCTCCTTCTTAAAGTTAAACAAAATTATTTC | 8 |
| Oligo 3 | GGCTAGCATGACTGGTGGACAGCAAATGGGTTGAAGAGCGTACATCA | 9 |

-continued

| | Sequence | SEQ ID NO: |
|---|---|---|
| Oligo 4 | CCGCCAGACCTGAAGAGCCGTGCACATATGATGTACGCTCTTCAACCC | 10 |
| Oligo 5 | GCTCTTCAGGTGCGGCCGCACATCATCATCATCATCATCATCACTAAGGA | 11 |
| Oligo 6 | GACATCTCGAGCGTTAGGATCCTTAGTGATGATGATGATGATGATGATG | 12 |
| Flanking Primer 1 | ATTCCCCTCTAGAAATAATTTTGTTTAACTTTAA | 13 |
| Flanking Primer 2 | GACATCTCGAGCGTTAGGATC | 14 |

The oligonucleotides were purchased from IDT and resuspended at a concentration of 12.5 μg/μL in water. For the first thermal cycling step, 2 μL of each oligonucleotide was combined with 0.25 μL of GoTaq polymerase (Promega, Madison, Wis.), 0.4 μL of 25 mM dNTP, 10 μL of 5× GoTaq buffer, and water for a 50 μL reaction. A 7 minute initial denaturing step at 94° C. was followed by 2 minutes of annealing at 54° C. and 3 minutes at 72° C. Seven amplification cycles were then carried out with 1.5 minutes at 94° C., 2 minutes at 54° C., and 3 minutes at 72° C., followed by a final extension step at 72° C. for 5 minutes. This reaction was followed by a standard PCR amplification using the flanking primers. The primers were resuspended in water at 0.25 μg/μL. One μL from the first reaction was combined with 0.5 μL of GoTaq, 0.8 μL of 25 mM dNTP, 20 μL 5× GoTaq buffer, 4 μL of each primer, and water for a 100 μL volume reaction. After an initial 5 minute denaturing step at 94° C., 25 cycles of amplification were carried out for 30 seconds at 94° C., 2 minutes at 54° C., and 1.5 minutes at 72° C., followed by a final 5 minute extension step at 72° C. The desired product band was isolated and purified by agarose gel electrophoresis.

The existing cloning region of the modified pET-41a plasmid was excised via double digestion using XbaI and XhoI enzymes. This region was replaced with the 179-bp oligonucleotide discussed above that was similarly digested with XbaI and XhoI to generate cohesive ends for ligation. This modified vector was designated MpET-41a. A fusion protein expressed in this vector will have a T7 tag at the N-terminus and an octahistidine tag at the C-terminus. The recipient vector was prepared by digesting the circular plasmid with SapI at 37° C. for 16 hours. This was followed by digestion with NdeI enzyme for 1 hour to linearize any undigested plasmid and then slab gel purification was used to isolate the desired vector band. Finally the vector was reacted with calf intestinal phosphatase (CIP) for an hour to minimize recircularization of the plasmid in subsequent ligation steps.

The IEGR (SEQ ID NO: 22) recognition site for Factor Xa can be inserted into existing plasmids that already contain the above mentioned sequence by designing a short sequence with compatible ends to replace the existing region between the NotI and XhoI restriction sites: 5'-CAGGTGCGGCCG-CAATCGAGGGAAGGCATCATCATCAT-CATCATCATCACTAAGGA TCCTAACGCTCGAGCAC-CAC-3' (SEQ ID NO: 15). This method was used to generate the PC-36 protein (267 aa sequence shown here is after GluC cleavage at amino acid E of the G-AAA-IEGR-H$_8$C-terminal affinity tag):

(SEQ ID NO: 16)
asmtggqqmgagtgsagagtgsagagtgsagagtgsagagtgragagtgs agagtgsagagtgsagagtgsagagtgsagagtgsagagtgsagagtgra gagtgsagagtgsagagtgsagagtgsagagtgsagagtgsagagtgsag agtgsagagtgsagagtgragagtgsagagtgsagagtgsagagtgsaga gtgsagagtgsagagtgsagagtgragagtgsagagtgsagagtgsagag tgsagagtgsagaaaie Alternatively, the 179-bp oligonucleotide can simply be redesigned to include the IEGR region (SEQ ID NO: 22) for new versions of the expression plasmid. The particular design used for the PC-72 protein results in a G-IEGR-AAA-H$_8$ affinity tag.

C. Protein Expression and Purification

Controlled cloning generated genes 756 and 1512 bases in length (encoding 36 and 72 repeats of the seven amino acid "monomer") from the 378-bp multimer gene (18 repeats) through two rounds of gene doubling. The multimer genes were excised from the pUC18 cloning vector via SapI digestion and were ligated into either the modified N-terminal decahistidine tag expression vector MpET-19b (Won, et al., *Macromolecules* 2002, 35, 8281-8287) (Novagen) or the MpET-41a recipient vector described above. Sequencing confirmed the identity of the resulting plasmid DNA before transferring the DNA into *E. coli* BLR(DE3) expression cells (Novagen) via heat shock. Protein expression was performed using Terrific Broth (EMD Biosciences, San Diego, Calif.) media at 37° C. under tetracycline (12.5 μg/mL) and either carbenicillin (50 μg/mL) or kanamycin (30 μg/ml) antibiotic selection for the MpET-19b and the MpET-41a vectors, respectively. One liter cultures were inoculated with 25 mL of a culture grown from a single colony in LB media overnight. After the cells reached OD$_{600}$=0.6-0.8, isopropyl-β-D-thiogalactoside (IPTG, U.S. Biologicals, Swampscott, Mass.) was added at a final concentration of 0.5 mM to induce protein synthesis. Cells were harvested by centrifugation at 6000 g at 4° C. for 12 minutes after 3 hours of additional growth time. The cell pellet was resuspended in denaturing buffer (8 M urea, 50 mM sodium phosphate, 300 mM NaCl at pH 7.8) and frozen overnight at −80° C. Cells were then lysed by ultrasonication for 2 minutes. The resulting cell lysate was centrifuged at 20,000 g at 4° C. for 45 minutes to pellet the cell debris. The clarified lysate was bound to Talon® cobalt-chelated resin (Clontech, Mountain View, Calif.) for 1 hour at room temperature prior to column purification. The resin was washed twice with 10 column volumes of the above mentioned denaturing buffer. The target protein was eluted using buffer containing an additional 150 mM imidazole (3 column volumes). Cell lysate, flow through, washes, and elutions were all analyzed on a discontinuous 12% SDS-PAGE gel. All gels were visualized with Coomassie staining. Negative zinc staining did not show better results than Coomassie. Elutions containing the target protein were combined and dialyzed three days against deionized water at 4° C. Finally the protein was lyophilized into a dry powder. When needed, the proteins were further purified using preparative reversed-phase HPLC on a Phenomenex Jupiter C18 column (10 µm, 300 Å, 21.2×250 mm) using a linear gradient of 5-95% solvent B in solvent A over 35 minutes at a flow rate of 15 mL/min. Solvent A is 0.1% trifluoroacetic acid (TFA) in water (v/v) and solvent B is 0.1% TFA in acetonitrile (v/v). Collected fractions were lyophilized to a dry powder, resuspended in water, pH adjusted to near neutral, and then lyophilized again.

The expressed proteins were designated PN-36 and PN-72 according to the number of 7 amino acid repeats. FIG. 2 is the SDS-PAGE gel for a purification of PN-72. The protein migrates higher on the gel than its expected molecular weight, likely due to the non-natural sequence and its lack of charged amino acids (besides the sparse arginine mutations and the His tag). Average protein yields ranged from 15-25 mg/L culture with the larger protein having lower yields.

D. Removal of N-Terminal Histidine Affinity Tag from the Expressed Fusion Protein For proteins expressed with the N-terminal His tag, removal of the affinity tag was accomplished through chemical cleavage at the N-terminal methionine residue (assuming no Met residues in the repetitive sequence) using cyanogen bromide in 70% formic acid for 24-48 hours (Gross, E., *Methods Enzymol.* 1967, 11, 238-255). Proteins were dissolved in the reaction mixture at a final concentration of ~1 mg/mL. Cyanogen bromide was added at approximately 5 mg/mg protein. After nitrogen purging, the entire mixture was covered with aluminum foil and gently mixed for several hours. A rotary evaporator was then used to remove volatiles and dry the solution under vacuum. The product was resuspended in water and lyophilized. A second column chromatography purification step with Talon® resin was performed to separate successfully cleaved protein from protein still containing the His tag.

The N-terminal His tag was removed by cyanogen bromide cleavage because of the presence of an existing enterokinase restriction site engineered into the tag design (DDDDK; SEQ ID NO: 17). The tag must be removed to prevent the lysine acting as another reactive site for the sulfo-SMCC conjugation to ssDNA. Additionally, the inclusion of multiple negatively charged amino acids would significantly reduce the effective drag of the protein drag-tag. Amino acid analysis of the two proteins matched expected molar compositions and analytical RP-HPLC appeared to confirm each protein was pure, consisting of a single peak on the chromatogram. Likewise, MALDI-TOF analysis showed the protein masses nearly matched expected values (Table 1) being only slightly higher than predicted. Circular dichroism spectroscopy confirmed that the proteins exhibited random coil conformations as designed.

TABLE 1

MALDI-TOF Analysis Results for PN Proteins

|  | Expected mass (Da) | Observed mass (Da) |
|---|---|---|
| PN-36 | 18405 | 18590 |
| PN-72 | 36736 | 37085 |

E. Assay of Reaction Conditions for Enzymatic Removal of C-Terminal Affinity Tag The C-terminal His tag includes an IEGR (SEQ ID NO: 22) recognition site for site-specific cleavage by Factor Xa (Novagen). Factor Xa to target protein ratios (unit: µg) of 1:100, 1:50, and 1:20 were tested. Ten micrograms of protein were digested by varying amounts of enzyme (0, 0.1, 0.2, 0.5 units) in a 50 µL reaction at 20° C. Ten microliters of sample were taken at 2, 4, 8, and 16 hour time intervals and immediately mixed with 10 µL of SDS-containing sample buffer for future SDS-PAGE analysis and to halt the cleavage reaction. Two micrograms of the control protein were digested with 0.1 units of enzyme for 16 hours. Test cleavage results were all analyzed by Western blot using a penta-His antibody (Qiagen) and anti-mouse IgG horseradish peroxidase (HRP) antibody (GE Healthcare, Piscataway, N.J.). Test digestions using endoproteinase GluC (New England Biolabs) as the protease were carried out at 25° C. in the provided reaction buffer using the protease to target protein (µg:µg) ratios of 1:100, 1:50, and 1:20. These reactions were similarly monitored over the course of 16 hours and the timepoints were analyzed by Western blot using the penta-His antibody.

F. General Protein Analysis and Characterization

Purified protein dissolved in water at 1 mg/mL was analyzed by reverse-phase HPLC on a Phenomenex Jupiter C18 column (5 µm, 300 Å, 2×250 mm) at a gradient of 5-95% acetonitrile to water with 0.1% TFA. Peaks were detected at 220 nm. A Voyager DE-PRO mass spectrometer (Analytical Services Laboratory, Northwestern University and Protein and Nucleic Acid Facility, Stanford University) was used for MALDI-TOF analysis of the protein using sinapinic acid as the matrix. Amino acid compositional analysis was performed by the W.M. Keck Facility at Yale University (New Haven, Conn.). Circular dichroism (CD) spectroscopy was conducted using a J-715 Jasco (Easton, Md.) spectrophotometer (Keck Biophysics Facility, Northwestern University). Data was collected between 185-280 nm using a 0.02 cm path length cuvette.

G. Protein Analysis and Characterization Using Free-Solution Conjugate Electrophoresis Protein polymers were further characterized by free-solution conjugate electrophoresis (FSCE) to determine the actual protein purity (Won, et al., *Electrophoresis* 2005, 26, 2138-2148). First, two oligonucleotides containing a thiol (—SH) functionality on the 5' terminus were purchased from IDT: a 23-base oligonucleotide (SH-GCA T*GT ATC TAT CAT CCA TCT CT; SEQ ID NO: 18) and a 30-base oligonucleotide (SH-CCT* TTT AGG GTT TTC CCA GTC ACG ACG TTG; SEQ ID NO: 19) were used (where T* indicates the dT-fluorescein). To reduce the DNA, 2 nmol of DNA primer was incubated with a 20:1 molar excess of Tris(2-carboxyethyl)phosphine (TCEP, Pierce Biotechnology, Rockford, Ill.) at 40° C. for 90 minutes in 20 µL of 70 mM sodium phosphate buffer, pH 7.2 (Meagher, et al., *Anal. Chem.* 2008, 80, 2842-2848). Protein polymers were activated at the N-terminus with the heterobifunctional crosslinker sulfosuccinimidyl 4(N-maleimidomethyl)cyclohexane-1-carboxylate (sulfo-SMCC, Pierce). A 10:1 molar excess of sulfo-SMCC was added to 1.2 mg of protein polymer in 80 µL of 100 mM sodium phosphate buffer, pH 7.2, and the mixture was vortexed for 1 hour at room temperature. Excess sulfo-SMCC was separated from the activated protein polymer drag-tag by gel filtration with a Centri-Sep column (Princeton Separations, Adelphia, N.J.). The activated, purified protein polymer was frozen, lyophilized, resuspended in water at 10 mg/mL concentration and stored at −80° C. until used (Meagher, et al., *Anal. Chem.* 2008, 80, 2842-2848). To conjugate the activated protein polymer to the reduced DNA, 90 pmol of DNA was mixed with 2.5 nmol of drag-tag to a final volume and concentration of 10 µL in 25 mM sodium phosphate buffer at pH 7.2. The mixture was then incubated at room temperature for 3-24 hours. A large excess of protein to DNA (typically 100-fold) is necessary to ensure nearly complete (>95%) conjugation of drag-tags to each DNA molecule (Meagher, et al., *Anal. Chem.* 2008, 80, 2842-2848; Coyne, et al., In *Handbook of Capillary and Microchip Electrophoresis and Associated Microtechniques,* 3rd ed.; Landers, J. P., Ed. CRC Press: New York, 2008; p 1567; Meagher, R. J. Ph.D. Dissertation, Northwestern University, Evanston, Ill., 2005).

An ABI 3100 Genetic Analyzer (Applied Biosystems, Foster City, Calif.) with a 16-capillary array of fused silica capillaries (50 µM inner diameter) and 4-color laser-induced fluorescence (LIF) detection using a 488 nm laser was used to analyze the protein polymer-DNA conjugates in free solution. Capillary electrophoresis separations of the conjugates were done in denaturing buffer consisting of 89 mM Tris (hydroxymethyl)aminomethane (Tris), 89 mM Tris(hydroxymethyl)methylaminopropanesulfonic acid (TAPS), 2 mM ethylenediaminetetraacetic acid (EDTA), and 7 M urea. A 0.5-3% (v/v) POP-5™ ("Performance Optimized Polymer") or POP-6™ polymer solution (Applied Biosystems) was added to the denaturing buffer as a dynamic wall coating agent to suppress electroosmotic flow and prevent adsorption to capillary walls. Capillaries with an effective length from inlet to detector of 36 cm were used for FSCE separations (total length 47 cm). Typical electrophoresis conditions include electrokinetic injection with a potential of 1-2 kV applied for 5-30 seconds and running voltage of 14.7 kV, at 55° C. (Coyne, et al., In *Handbook of Capillary and Microchip Electrophoresis and Associated Microtechniques,* 3rd ed.; Landers, J. P., Ed. CRC Press: New York, 2008; p 1567; Meagher, R. J. Ph.D. Dissertation, Northwestern University, Evanston, Ill., 2005; Meagher, et al., *Electrophoresis* 2006, 27, 1702-1712).

H. Characterization of N-Terminal His Tag Protein by FSCE

Figure 3A:
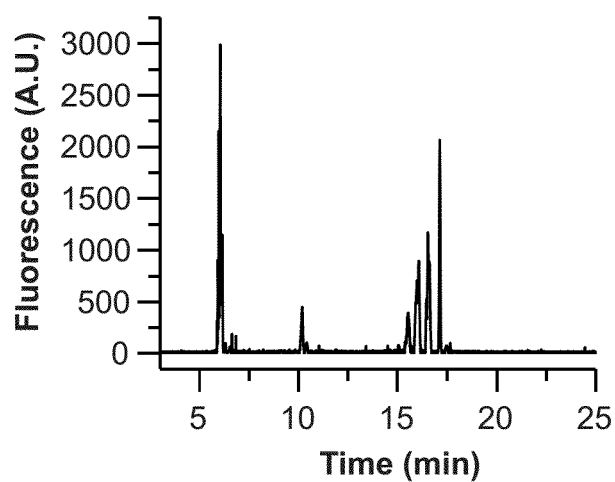
FIGS. 3A and 3B depict results of the free-solution capillary electrophoresis of drag-tag-DNA conjugates for (3A) a protein preparation code-named "PN-36", comprising 253 amino acids; and (3B) a protein preparation code-named "PN-72", comprising 505 amino acids, using a 30-base oligonucleotide primer. The analysis was performed using an ABI 3100 capillary array electrophoresis (CAE) instrument that offers highly sensitive, multi-color, laser-induced fluorescence (LIF) detection, outfitted with an array of 36-cm long fused silica (glass) capillaries with 50 μm inner diameters (ID) on average. Electrophoresis was performed in an aqueous buffer comprising 50 mM Tris(hydroxymethyl)aminomethane ("Tris"), 50 mM N-Tris(hydroxymethyl)methyl-3-aminopropane sulfonic acid ("TAPS"), and 2 mM EDTA ("0.5×TTE") buffer with 7M urea, which also contained 3% (v/v) of "POPS" polymer solution from Applied Biosystems Inc. ("ABI", a Life Technologies company), which provides "dynamic coating" of capillaries and hence, the suppression of electroosmotic flow), utilizing an electrokinetic sample injection scheme with an applied field of 1 kV total, for one second. The CAE separation of the FSCE bioconjugates was carried out at a fixed temperature of at 55° C., using an applied electric field of 312 V/cm.
Figure 3B:
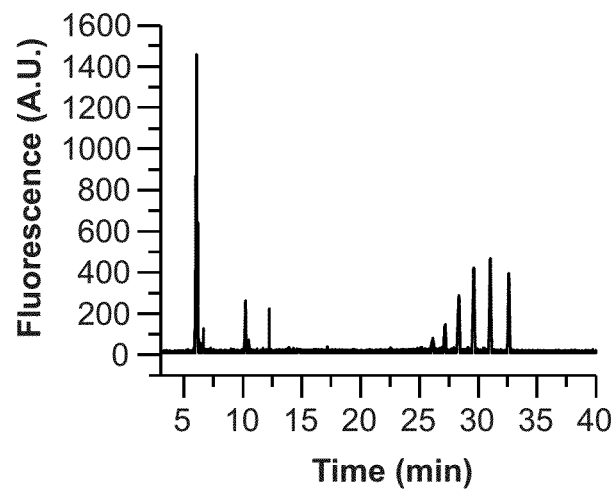

Protein polymers were further characterized by free-solution conjugate electrophoresis to determine the actual protein monodispersity and their suitability as drag-tags for free-solution DNA sequencing. PN-36 and PN-72 were conjugated to ssDNA primers and analyzed by free solution capillary electrophoresis. No polymer matrix was utilized for the DNA separation beyond the small amount used as a dynamic wall coating agent. FIG. 3 shows the FSCE electropherograms of PN-36 and PN-72. The peak on the far left of each electropherogram corresponds to the free (unconjugated) DNA whereas the larger peak(s) on the far right corresponds to the drag-tag-DNA conjugate(s), which eluted later due to attachment of the drag-tag. The larger size and increased number of arginines of PN-72 lead to greater drag on the attached DNA and eluted several minutes later in comparison to the DNA conjugated to PN-36. The smaller protein PN-18 displayed relatively minor impurities associated with a single peak (Meagher, et al., *Anal. Chem.* 2008, 80, 2842-2848) but multiple, distinct peaks of varying heights were observed in the electropherograms for PN-36 and PN-72, indicating that the attached protein polymer drag-tag was, in fact, rather heterogeneous. The polydispersity was more pronounced for the largest protein, PN-72, and appeared related to the length of the protein polymer. The number of distinct bioconjugate peaks increased from four to six. Additionally, the width of the distribution of peaks increased from 1.7 minutes in FIG. 3A to 6.6 minutes in FIG. 3B. Proteins in which the N-terminal His tag was removed by the enterokinase protease instead of chemical cleavage by cyanogen bromide, exhibited similar profiles by FSCE, indicating that the method of affinity tag removal was likely not the main contributing factor to the observed heterogeneity.

I. C-Terminal His Tag Protein Expression and Purification

The highly repetitive nature of protein polymer amino acid sequences can be problematic for protein expression if the desire is to obtain completely monodisperse product. Premature protein truncation during synthesis has been previously observed for silk-based protein polymers (Fahnestock, S. R.; Irwin, S. L., *Appl. Microbiol. Biotechnol.* 1997, 47, 23-32; Huang, et al., *J. Biol. Chem.* 2003, 278, 46117-46123). Termination errors in protein synthesis may be due to depletion of available tRNA pools for certain codons, particularly any that are of low usage in *E. coli* synthesis (Fahnestock, S. R.; Irwin, S. L., *Appl. Microbiol. Biotechnol.* 1997, 47, 23-32; Robinson, et al., *Nucleic Acids Res.* 1984, 12, 6663-6671; Rosenberg, et al., *J. Bacteriol.* 1993, 175, 716-722; Kane, J. F., *Curr. Opin. Biotechnol.* 1995, 6, 494-500). Additionally the Gene 1 sequence is approximately 43% glycine and 28% alanine. Therefore, it is likely that even relatively abundant species of tRNA can become depleted as well, despite utilizing a variety of Gly and Ala codons in the gene sequence. As a further precaution, protein expression is performed in the BLR(DE3) cell strain, which has an additional recombinase gene (recA) knocked out compared to the more commonly utilized BL21 strain. Thus, potential repetitive gene recombination events are reduced or eliminated that could lengthen or shorten the gene within the plasmid, another possible source of heterogeneity (Prince, et al., *Biochemistry* 1995, 34, 10879-10885; Fahnestock, S. R.; Irwin, S. L., *Appl. Microbiol. Biotechnol.* 1997, 47, 23-32).

The 756 and 1512 bp genes (36 and 72 repeats of the seven amino acid "monomer") used above for expression were also inserted into MpET-41a and expressed in *E. coli* BLR(DE3) cells. A T7 tag was included at the N-terminus to enhance protein expression. These new proteins were designated PC-36 and PC-72. Although the sizes of the repetitive regions are comparable to that of the PN proteins, the addition of the T7 tag actually makes these proteins slightly larger. Specifically, PC-36 and PC-72 have molecular weights of 21.1 kDa and 39.4 kDa, respectively, when both the T7 tag and the His tag are attached. Protein yields ranged from 5-10 mg/L culture depending on the size of the protein being expressed. If truncation was occurring then only full length expressed proteins would have the C-terminal His tag and be isolated and purified by affinity chromatography. A reduction in yield would be expected with the exclusion of incomplete proteins from the purified product. Proteins expressed with the C-terminal His tag and no N-terminal T7 tag had even poorer yields in comparison and were not studied further (data not shown). Most likely due to the lower overall expression levels of the desired proteins using a C-terminal His tag, visible amounts of native protein contaminants were observed in the elution fractions by SDS-PAGE after affinity chromatography. Preparative RP-HPLC on a C18 column was used as a second purification step to remove these impurities. Although RP-HPLC cannot readily distinguish between protein polymers of widely varying sizes, the protein polymers do separate well from typically more hydrophobic natural *E. coli* proteins. MALDI-TOF confirmed the molecular masses of the proteins.

J. Characterization of C-Terminal His Tag Protein by FSCE

Figure 4:
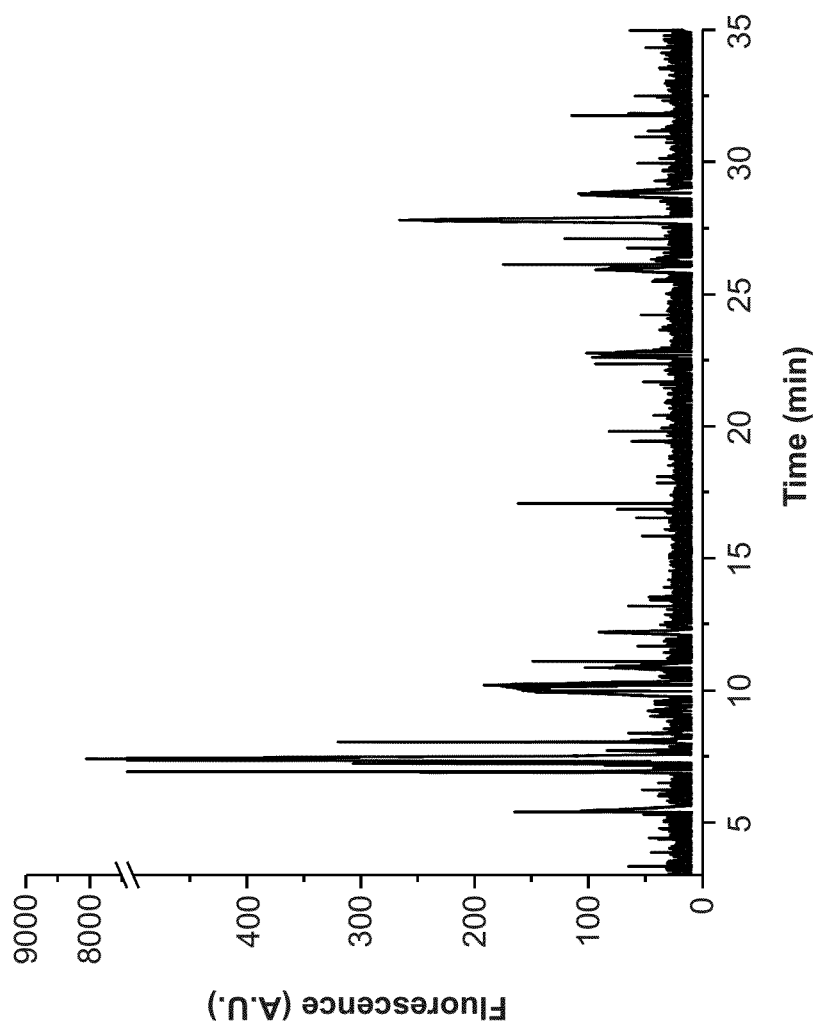
FIG. 4 depicts the free-solution capillary electrophoresis of drag-tag-DNA conjugates for a protein preparation code-named "PC-36", comprising 273 amino acids, using a 23-base oligonucleotide primer with a fluorescent label. The analysis was performed in a similar manner and under similar conditions to that described in FIG. 3 in detail; vide supra. This separation was performed using an ABI 3100 CAE instrument with the 36-cm capillary array installed, which uses 50-μm ID capillaries, and 0.5×TTE, 7M urea, 0.5% (v/v) POP6 was chosen for the electrophoresis buffer, as well as a 1 kV/20 second electrokinetic injection and an applied electric field of 312 V/cm, with separations run at 55° C.

Since neither the T7 tag nor the C-terminal His tag contain any lysine residues, neither tag was removed prior to conjugation to thiolated ssDNA using the heterobifunctional linker, sulfo-SMCC. However, analysis of the bioconjugates by free solution capillary electrophoresis showed unexpectedly poor conjugation yields. FIG. 4, the FSCE result for PC-36, shows that the free DNA peak is more than 10 times stronger in fluorescence intensity than the largest conjugate peak, indicating a very poor conjugation reaction yield in which most of the DNA did not attach to the protein polymer. This is in contrast to FIG. 3A, the FSCE result for PN-36, which shows a free DNA peak only 1.5 times greater than the largest conjugate peak. Although FIG. 4 does not demonstrate a noticeable improvement in protein purity when expressed with a C-terminal affinity tag, the peak pattern is distinctly different in comparison to previous results.

A plausible explanation for the observed low conjugation efficiency is that histidine is reacting with the sulfo-SMCC reagent during the conjugation step. Histidine can react with N-hydroxysuccinimide (NHS) esters, effectively accelerating the rate of hydrolysis of the NHS groups in solution (Mattson, et al., *Mol. Biol. Rep.* 1993, 17, 167-183; Cuatrecasas, et al., *Biochemistry* 1972, 11, 2291-2299). The unstable reaction product that is formed rapidly hydrolyzes. Typically, the NHS-ester reaction is performed first (i.e., drag-tag activation) to minimize hydrolysis as it is less resistant to hydrolysis than the maleimide group in sulfo-SMCC (Mattson, et al., *Mol. Biol. Rep.* 1993, 17, 167-183). The histidines on the affinity tag may essentially be accelerating the hydrolysis of the reagent. Unlike a natural protein, there is only a single primary amine at the N-terminus of the protein polymer which may not be a strong enough nucleophile compared to the eight adjacent histidines at the C-terminus. Thus the sulfo-SMCC reagent preferentially reacts with the histidines, accelerating hydrolysis of the crosslinker and thus rendering it ineffective for conjugation as the crosslinker is now two separate molecules. Higher concentrations of sulfo-SMCC could be used to overcome this behavior. However, 100-fold excess of sulfo-SMCC reagent as opposed to the standard 10-fold molar excess showed no noticeable improvement in conjugation efficiency. It should also be noted that other commonly used small affinity tags such as FLAG (DYKDDDDK; SEQ ID NO: 20) or Strep tag (WSHPQFEK; SEQ ID NO: 20) are of less use than the His tag due to the presence of lysines in those sequences.

K. Removal of C-Terminal Affinity Tag

It would be advantageous to remove the C-terminal affinity tag completely to eliminate any possible side reactions that are causing either low conjugation yields or additional bioconjugate peaks to appear in the electropherogram. However, insertion of a methionine to act as a reactive site for cyanogen bromide cleavage was not as effective in this situation as it was for removal of the N-terminal affinity tag. After the cleavage reaction, the Met residue becomes the new C-terminus of the protein polymer. As part of the reaction, the methionine residue is converted into an equilibrium mixture of homoserine and homoserine lactone, which would result in at least two distinct peaks in a FSCE analysis that is performed at pH 8.5 (Gross, E., *Methods Enzymol.* 1967, 11, 238-255; Kuliopulos, et al., *J. Am. Chem. Soc.* 1994, 116, 4599-4607; Armstrong, M. D., *J. Am. Chem. Soc.* 1949, 71, 3399-3402; Murphy, et al., *Anal. Chem.* 1995, 67, 1644-1645; Lee, et al., *Methods Enzymol.* 1990, 193, 361-374). Alternatively, site-specific proteases are commonly used to remove N-terminal affinity tags. However, enzymatic removal of a C-terminal affinity tag will result in part or all of the protease recognition sequence becoming the new C-terminus of the cleaved protein.

The protease Factor Xa was selected as only four additional amino acids (IEGR; SEQ ID NO: 22) from its recognition site would be added to the C-terminus of the cleaved protein (cleavage site is after Arg). Three of the amino acids have already been used in past or present protein polymer designs and are not expected to cause complications. Only one hydrophobic residue (isoleucine) is added to the protein. The negative charge of the glutamic acid is counteracted by the addition of a positively charged arginine. Adding two charged residues may also balance out the hydrophobicity of the isoleucine. Test cleavages were performed to determine appropriate reaction conditions for a larger scale reaction. The protein polymer, in general, does not stain well by Coomassie Blue due to its near neutral sequence and at the low amounts used for these the studies, the proteins were unable to be visualized by SDS-PAGE. Therefore, the results were analyzed by the more sensitive Western blot method for Factor Xa to target protein ratios of 1:100, 1:50, and 1:20 (unit: µg) at 2, 4, 8, and 16 hour timepoints at 20° C. The Western blot can only identify protein bands with a His tag still attached using the penta-His antibody. Addition of the protease unexpectedly showed evidence of digestion of the PC-36 target protein into multiple distinct bands. These bands most likely resulted from recognition of the four Gly-Arg mutation sites in the PC-36 sequence as cleavage sites by the enzyme. A reduction in temperature to 4° C. or 10-fold dilution of the protease concentration either completely halted enzymatic activity or failed to prevent non-specific cleavage.

Figure 6:
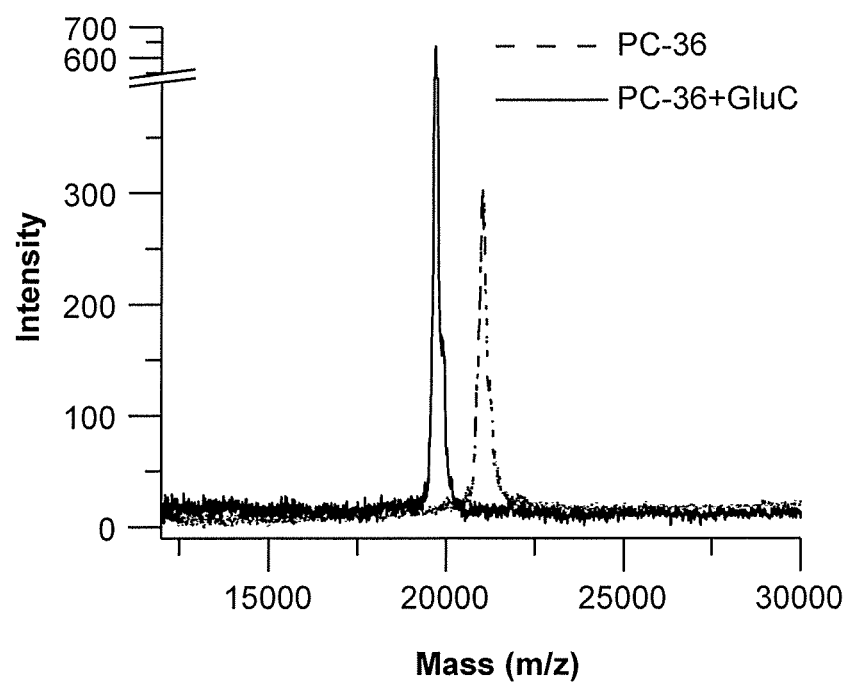
FIG. 6 depicts an overlay of the results of the MALDI-TOF analysis of the "PC-36" protein preparation, before and after digestion of the proteins by added endoproteinase GluC.

Fortuitously, the addition of the IEGR (SEQ ID NO: 22) recognition sequence also introduced a unique glutamic acid residue to the protein sequence. Endoproteinase GluC is a serine protease that can cleave specifically after Glu residues. This enzyme is typically used for peptide digestion and identification using mass spectrometry and not for affinity tag cleavage since natural proteins commonly contain Glu residues. The version sold by New England BioLabs includes a histidine tag at its C-terminus. Consequently, after protease digestion, the cleaved His tag, uncleaved protein, and the protease can all be removed in a single chromatographic step from the cleaved protein. Digestion was done at 25° C. in the provided reaction buffer using the protease to target protein (µg:µg) ratios of 1:100, 1:50, and 1:20. These reactions were monitored over the course of 16 hours and the results were analyzed by Western blot (FIGS. 5A-C). Cleavage was successful in less than 8 hours for all protease concentrations tested. Endoproteinase GluC has a different mass than the PC-36 protein and thus they are easily distinguishable on the blot. Additionally, the protease band remains essentially constant for each concentration. Curiously, faint bands are detected in all three 16 hour reactions. These unexpected bands may be associated with side reactions of the long incubation time such as autolysis of the protease. A larger scale reaction was performed using 50 µg of endoproteinase GluC and 5 mg of PC-36 for 6 hours at 25° C. After dialysis and lyophilization, the reaction mixture was resuspended in denaturing buffer and purified on Talon® resin. However, in this situation the flow-through and wash fractions were collected as they contained the desired, completely cleaved protein polymer. MALDI-TOF confirmed the affinity tag was successfully removed by the enzyme as evidenced by the mass shift shown in FIG. 6 comparing measurements made before and after the reaction. Approximately 5 mg of material was recovered in the flow-through fraction, indicating complete removal of the affinity tag.

The same endoproteinase GluC treatment was applied to the larger PC-72 protein. Western blot analysis of the test cleavages (FIG. 5D-G) show the presence of multiple bands upon addition of the protease but the PC-72 protein itself was stable in the reaction buffer over the entire 12 hours if no protease was added. Interestingly, these bands were not as well-defined as those resulting from Factor Xa digestion, indicating that non-specific cleavage was likely occurring at multiple locations and not specifically at Gly-Arg regions. Six milligrams of PC-72 was reacted for 12 hours at 25° C. using a 1:20 µg/µg ratio of protease to PC-72. The reaction was purified by column chromatography. All material was recovered in the flow through and wash fractions, indicating complete removal of the affinity tag.

L. Analysis by FSCE of Endoproteinase GluC-Digested Proteins

Figure 7A:
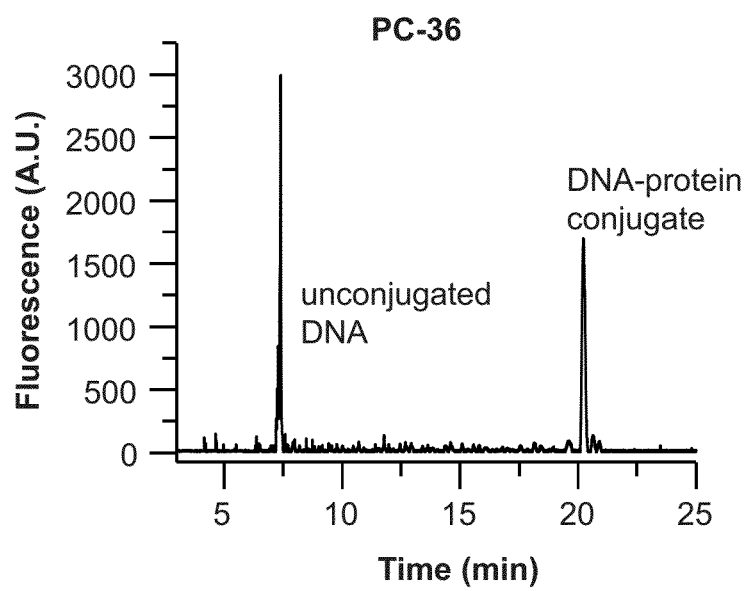
FIGS. 7A and 7B depict (A) free-solution capillary electrophoresis of drag-tag-DNA conjugates for PC-36, with the long, multi-histidine-containing ("His") affinity tag removed (267 amino acids), and using a 30-base fluorescently labeled oligonucleotide primer; and (B) free-solution capillary electrophoresis of drag-tag-DNA conjugates for PC-72 with His tag removed (516 amino acids), using a 30-base, fluorescently labeled DNA primer. As above: ABI 3100 CAE instrument, 36-cm array with 50 μm ID capillaries, 0.5×TTE, 7M urea, 0.5% (v/v) POPE, 1 kV/20 second injection, 312 V/cm, 55° C.

The cleaved PC-36 protein was conjugated via sulfo-SMCC to ssDNA primer and analyzed by free solution capillary electrophoresis. FIG. 7A is an electropherogram showing that the bioconjugate is monodisperse and that the conjugation efficiency has significantly improved with the removal of the histidine-containing affinity tag. A couple minor peaks of unknown origin can be observed in the electropherogram. These may be due to protease cleavage at other sites along the affinity tag such as the G or R residues adjacent to the glutamic acid. Overall the PC-36 protein is significantly more monodisperse than the version previously expressed using an N-terminal affinity tag when both are analyzed by FSCE (FIG. 3A). This protein has double the mass and hydrodynamic drag of the PN-18 protein used previously for successful FSCE DNA sequencing and is expected to produce even longer sequencing reads with its improved ability (i.e., greater hydrodynamic drag) to separate larger DNA sizes in free solution.

Figure 7B:
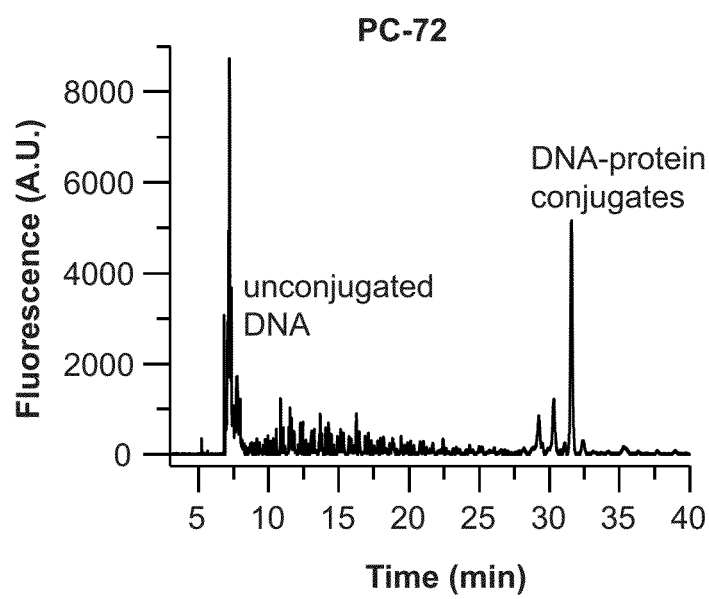

The cleaved PC-72 was also conjugated to DNA and analyzed by FSCE (FIG. 7B). At least two smaller peaks are clearly visible that elute prior to the main peak. The baseline is also noisier compared to the PC-36 analysis, likely the by-products of non-specific enzymatic cleavage. As expected, the larger size of PC-72 allows it to better separate two different sizes of DNA by FSCE in comparison to PC-36. Although not as monodisperse as the GluC-cleaved PC-36 protein, the monodispersity is noticeably improved over FIG. 3B. MALDI-TOF matches the expected mass of the PC-72 protein before and after removal of the His tag. However, the protein polymer appears as a single, broad peak by MALDI-TOF that could not be further resolved. This is typical for its size (38 kDa), regardless of whether the protein is expressed with an N- or C-terminal affinity tag. It is apparent that removal of the affinity tag by endoproteinase GluC has drawbacks when applied to proteins much larger than PC-36 and further studies are needed to identify the cause of and reduce the polydispersity observed in the PC-72 protein.

The 1:20 through 1:100 (w/w) ratio of enzyme to substrate used for removal of the His tag is within the recommended range for this protease. It is not expected that the random coil structure of these proteins is preventing protease accessibility. A reduction in reaction time to 6 hours from 12 hours had no noticeable effect on the final FSCE analysis for PC-72 nor did reducing the enzyme concentration five-fold to match the reaction conditions used for PC-36. In other words, using the same reaction conditions as the PC-36 digestion along with the same mass of protein (albeit half the molar amount), did not affect results beyond lowering the yield of fully cleaved protein. Addition of more protease may allow for these side reactions to proceed further towards completion, thus reducing the size of the secondary peaks but likely also reducing the final amount of the main peak.

M. Conjugation of Drag-Tag and Sequencing Sample Preparation

PC-36 protein drag-tag was conjugated to DNA sequencing primer (5'-X1-GTT TTC CCA GTC ACG AC; SEQ ID NO: 23; Integrated DNA Technologies, Coralville, Iowa), via the heterobifunctional linker molecule sulfo-SMCC as described above. To test the conjugation of the drag-tag to the sequencing primer, a single-base extension (SBE) assay was performed. A 2.2 pmol amount of DNA-drag-tag conjugate, 62.5 ng of M13 mp18 ssDNA template (New England Biolabs, Ipswich, Mass.), 5.0 µL of SNaPshot Multiplex mix (Applied Biosystems, Foster City, Calif.), and water were mixed to a total volume of 10 µL. The reaction was heated at 96° C. for 1 min then cycled 25 times: 96° C. for 10 s, 50° C. for 5 s, and 60° C. for 30 s (Eppendorf Mastercycler Gradient). The sample was purified with a CentriSep column, denatured at 95° C. for 2 min, and snap-cooled on ice for 5-10 min. To create the sequencing sample, the following was mixed: 8.4 pmol of sequencing primer plus drag-tag, 0.16 µg of M13 mp18 ssDNA template, 8.0 µL of BigDye terminator v1.1 cycle sequencing mix (ABI), and water to a total volume of 20 µL. After incubation at 96° C. for 1 min, the sequencing reaction was cycled 36 times (96° C. for 10 s, 50° C. for 5 s, 60° C. for 30 s to 2 min). The sample was purified, denatured, and snap-cooled.

Separations of drag-tags plus ssDNA oligomers or DNA sequencing fragments were performed using an Applied Biosystems Prism 3100 Genetic Analyzer with four-color LIF detection. The 16-capillary array of bare fused-silica capillaries has an inlet-to-detector length of 36 cm (total length 47 cm) and 50 µm ID. Electrophoresis was performed in 1×TTE buffer (89 mM Tris, 89 mM TAPS, 2 mM EDTA) plus 7 M urea and a 1:200 dilution of POP-6 ("Performance-Optimized Polymer", ABI) for dynamic wall-coating (Hert, et al., *Electrophoresis* 2008, 29, 4618-4626; Won, et al., *Macromolecules* 2002, 35, 8281-8287; Huang, et al., *J. Biol. Chem.* 2003, 278, 46117-46123; Robinson, et al., *Nucleic Acids Res.* 1984, 12, 6663-6671). The drag-tagged samples were introduced into the capillary array by electrokinetic injection at 22 V/cm for 20 s, and the separation was carried out at 55° C. with an electric field strength of 62-312 V/cm (3-15 kV applied voltage). Fresh buffer was flushed into the array between each run, and reservoirs were refilled every 1-5 runs.

Figure 13A:
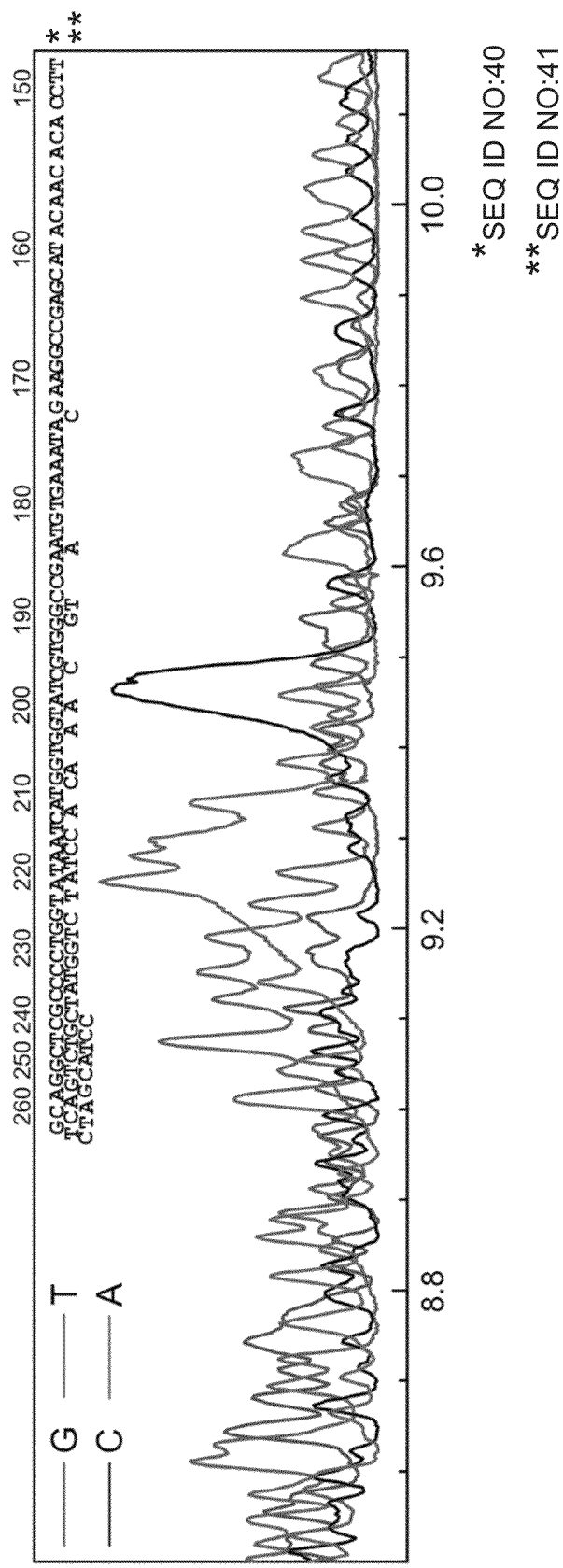
FIGS. 13A and 13B depict the four-color sequencing electropherogram with a 36mer drag-tag PC-36 (267-aa); 265 bases are resolved by electrophoresis without a sieving polymer.
Figure 13B:
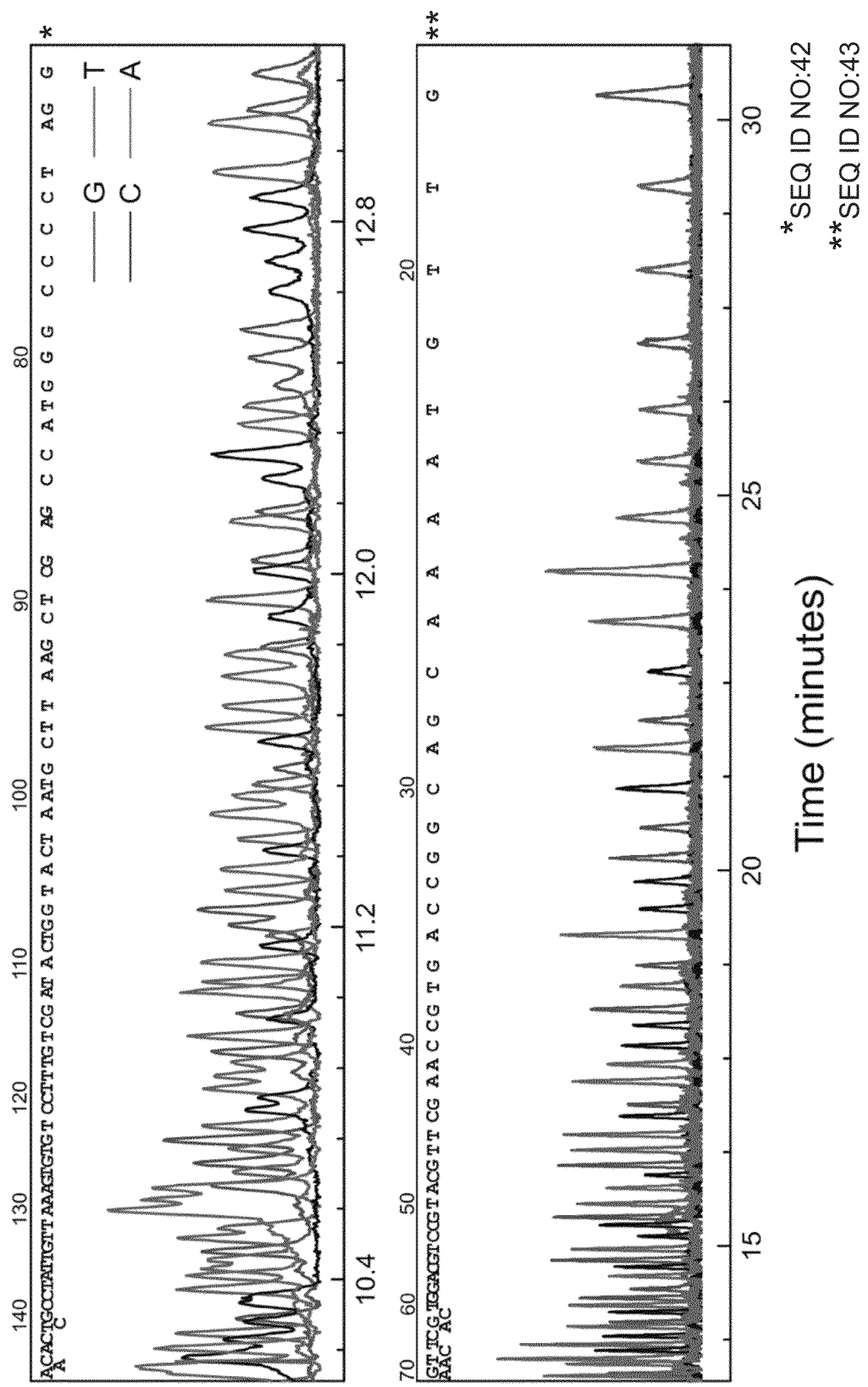

Sequencing fragments were generated using the sequencing primer conjugated to the PC-36 drag-tag. The sequencing fragments were successfully separated by free-solution electrophoresis with no entangled polymer network present. Representative electropherograms are shown in FIG. 13 with separations at 312 V/cm. The smallest fragment (18 bases) elutes last while the largest fragments migrate fastest; the sequence is read "backwards," starting at the right side of the bottom panel of the figures. The sequencing electropherograms are essentially "raw" data; the only corrections made were spectral deconvolution of the dyes (automatically performed by the ABI 3100) and baseline subtraction. No corrections have been made to normalize for peak height or mobility shifts induced by different dyes. The sequence obtained with the 36mer drag-tag was determined to M=170 bases before repeated peaks become unresolved or peaks begin to overlap or become out of order due to different mobility shifts of the four dye molecules. Using the known sequence of the template for alignment, sequencing peaks separated with the 36mer drag-tag can be read to M=265 bases. (Sequencing peaks separated with the 27mer protein are distinguishable to M=210 bases.) The 36mer drag-tag is twice the length of the previously reported 18mer has an α more than double, and is approximately a 47% increase in read length (Meagher, et al., *Anal. Chem.* 2008, 80, 2842-2848). This is the longest sequencing read ever recorded by FSCE separations, and longer drag-tags are expected to give even longer reads. The protein polymer drag-tags were incorporated into the traditional Sanger reaction with ease, which provides a notable advantage. The primers were conjugated to the drag-tags and included in the reaction without modification to the standard cycling protocol. While the previous study used the SNaPshot kit, this study used the BigDye kit (both ABI), demonstrating that the method is kit-independent (Meagher, et al., *Anal. Chem.* 2008, 80, 2842-2848). Both yield sequencing peaks with no sign of degradation from the presence of the drag-tag. This advantage appears to be limited to proteins <390 aa, as neither the SBE nor the sequencing reaction proceeded with the two largest drag-tags conjugated to the primer (54mer with 390-aa, 72mer with 516-aa). The presence of these large proteins appended to the 5' end of the was then digested at 37° C. by EarI. The fully cleaved 90-bp fragment was isolated and purified using agarose gel electrophoresis and the QIAEX II Gel Extraction Kit (Qiagen, Valencia, Calif.). Multimers of the gene were then generated by self-ligation using T4 DNA ligase. These multimers were inserted into a modified pUC18 cloning vector containing flanking SapI sites in accordance with the controlled cloning method. The plasmids were transformed via heat shock into NovaBlue competent cells (Novagen, Madison, Wis.). The resulting colonies were screened by DNA sequencing to verify the identity and size of the insert DNA.

Two multimer genes cloned from R15 were selected: a 540-bp gene R15-6 with six repeats of R15, and a 324-bp gene with three repeats of a mutant version of R15. The mutation inserted a sequence encoding GTAGSA after the second Ala, resulting in the average arginine spacing increasing to one per 18 amino acid residues. Therefore, this new gene was renamed R18-3. The amino acid sequences encoded by R15-6 and R18-3, respectively, are (GTAGSATGAGSAG-SRGTAGSGATGASGTGR)$_6$ (identified as SEQ ID NO: 24) and (GTAGSAGTAGSATGAGSAGSRGTAGS-GATGASGTGR)$_3$ (identified as SEQ ID NO: 25) These genes were either inserted into the MpET-41a vector for expression with a C-terminal His tag or into the modified pTXB1 for expression with a C-terminal intein-CBD tag. The intein CBD tag contains a GA sequence added to the end of the R18-3 sequence to improve intein cleavage efficiency.

B. General Method: Generation of Expression Vector with C-Terminal Intein-Tag

The pTXB1 vector was modified to be adapted to the controlled cloning system for producing protein polymer drag-tags. A 54-bp adapter oligonucleotide (FIG. 9) containing a newly designed cloning region (5'-CATATGGGT-TGAAGAGCCGTACATGAGCTCTG-CACGGGCTCTTCAGGTGCGTGC-3'; SEQ ID NO: 26) was generated by annealing two complementary single-stranded oligonucleotides below (Stanford University Protein and Nucleic Acid Facility).

```
Forward Oligo 5'-TATGGGTTGAAGAGCCGTACATGAGCTCTGCACGGGCTCTTCAGGTGCG-3'

Reverse Oligo 5'-GCACGCACCTGAAGAGCCCGTGCAGAGCTCATGTACGGCTCTTCAACCCA-3'
``` primer inhibited the Sanger reaction, likely from some type of steric hindrance (the drag-tag could have blocked the hybridization of primer to template, or binding of polymerase to primer-template hybrid, or a combination of both).

Example 2

A. Gene Generation for Repetitive Protein Polymers

The synthetic "monomer" gene R15, a 113-bp single-stranded synthetic oligonucleotide, was designed to encode a thirty-amino acid sequence consisting of Ala, Gly, Thr, and Ser, with 1 Arg per 15 amino acids (i.e., 30 amino acids including 2 Arg residues per ssDNA). Two evenly spaced arginine residues in the sequence of gene R15 were used to introduce cationic charges. The gene and amino acid sequence are shown in FIG. 8. The oligonucleotide was purchased from Integrated DNA Technologies (IDT, Coralville, Iowa) and was PCR-amplified using high fidelity Pfu DNA polymerase (Stratagene, La Jolla, Calif.). The PCR product The annealing reaction was conducted with 12.5 µM of each ssDNA. After denaturing at 95° C. for 5 min, the two ssDNA were annealed with a temperature ramping protocol that decreased from 85° C. to 75° C. in 30 min and then decreased to 4° C. immediately afterwards. The Multiple Cloning Site (MCS) of the original pTXB1 vector was removed by double digestion using two restriction enzymes, NdeI and SapI. The 54-bp adapter DNA was inserted to create the modified pTXB1 vector, MpTXB1. The new cloning region contained two SapI recognition sites to adapt the vector to the controlled cloning system. An alanine codon was included just before the first codon of the intein sequences to yield higher on-column cleavage activity (according to the accompanying instruction manual for the IMPACT system). The recipient vector was prepared by digesting the circular plasmid with SapI at 37° C. Slab gel purification was performed to isolate the desired vector band. Finally, the vector was reacted with calf intestinal phosphatase (CIP) for an hour at 37° C. to minimize recircularization of the plasmid in subsequent ligation steps.

C. General Method: Protein Expression and Purification Via an Intein-Mediated System The desired genes of the protein polymers were excised from the pUC18 cloning vector via SapI digestion and were ligated into the MpTXB1 recipient vector. The identity of the resulting plasmid DNA was confirmed by sequencing. Plasmids were transformed into *E. coli* BLR(DE3) expression cells (Novagen) via heat shock. Protein expression was performed using Terrific Broth media (EMD Biosciences, San Diego, Calif.) under tetracycline (12.5 μg/mL) and carbenicillin (50 μg/mL) antibiotic selection. A 25 mL overnight culture grown in LB media was inoculated into one liter of Terrific Broth and grown at 37° C. After the cells reached $OD_{600}$=0.4, the temperature was decreased to 16° C. and isopropyl-O-D-thiogalactoside (IPTG, U.S. Biologicals, Swampscott, Mass.) was added at a final concentration of 0.4 mM to induce protein synthesis. After 20 hours of additional growth time at 16° C., cells were harvested by centrifugation at 6000 g at 4° C. for 12 minutes.

Affinity purification and on-column cleavage was performed according to the protocols in the instruction manual for the IMPACT system with a couple of modifications in order to obtain better results for these proteins. First, the concentration of NaCl in the column buffer was decreased from 500 mM to 350 mM to decrease the ionic strength of the buffer and reduce the presence of impurities. Second, the clarified cell extract was gently mixed with prepared chitin beads at 4° C. for 2 hours before loading onto the column for enhanced binding. Overnight on-column cleavage was conducted at 25° C. with 50 mM DTT added to the column buffer. Cell lysate, flow through, washes, samples before DTT treatment, elutions and samples after elution were all analyzed on a discontinuous 12% SDS-PAGE gel. Elutions containing the target protein were combined and dialyzed three days against deionized water at 4° C. Finally the protein was lyophilized into a dry powder.

To further purify the proteins and achieve completely monodisperse drag-tags for FSCE applications, reversed-phase HPLC was performed after affinity purification to eliminate co-eluted intein-tag as well as other impurities. Approximately 10-15 mg of protein was dissolved in 4 mL water and, then loaded onto a Phenomenex Jupiter C18 column (10 μm, 300 Å, 21.2×250 mm). A linear gradient of 5-95% solvent B (0.1% TFA in acetonitrile (ACN) (v/v)) in solvent A (0.1% trifluoroacetic acid (TFA) in water (v/v)) over 35 minutes at a flow rate of 15 mL/min was used. The target protein eluted at approximately 35% ACN. Fractions were lyophilized, resuspended in water and pH adjusted to near neutral, and then lyophilized again.

D. R15-6 C-Terminal His Tag Polypeptides

The R15-6 gene was first inserted into MpET-41a for expression with a C-terminal His tag. A T7 tag MASMTG-GQQMG (SEQ ID NO: 3) was also included at the N-terminus to enhance protein expression. Protein expression is performed in the BLR(DE3) cell strain, which has an additional recombinase gene knocked out to prevent potential repetitive gene recombination events. The protein was purified on Talon® cobalt resin under denaturing conditions, and the fractions were analyzed by SDS-PAGE. The expressed protein was designated CR15-6 with the C indicating the C-terminal His tag was used in its production. Average protein yield is about 10 mg/L culture. Trace amounts of native protein contaminants were observed in the elution fractions. Preparative RP-HPLC on a C18 column was used as a second purification step to remove these impurities since the non-natural protein polymers separate efficiently from the typically more hydrophobic natural *E. coli* proteins. MALDI-TOF confirmed the molecular mass of the protein.

Endoproteinase GluC was chosen for His tag removal as in previous work. Digestion was performed at 25° C. for 6 hours in the provided reaction buffer using 50 μg enzyme for 5 mg of the target protein (CR15-6). After protease digestion, the cleaved His tag, uncleaved protein, and the protease (which also has a His tag) were removed from the cleaved protein in a single chromatographic step. SDS-PAGE confirmed the successful removal of the His tag. Almost all of the starting material was recovered from flow-through and wash fractions, indicating complete removal of the affinity tag.

Figure 10:
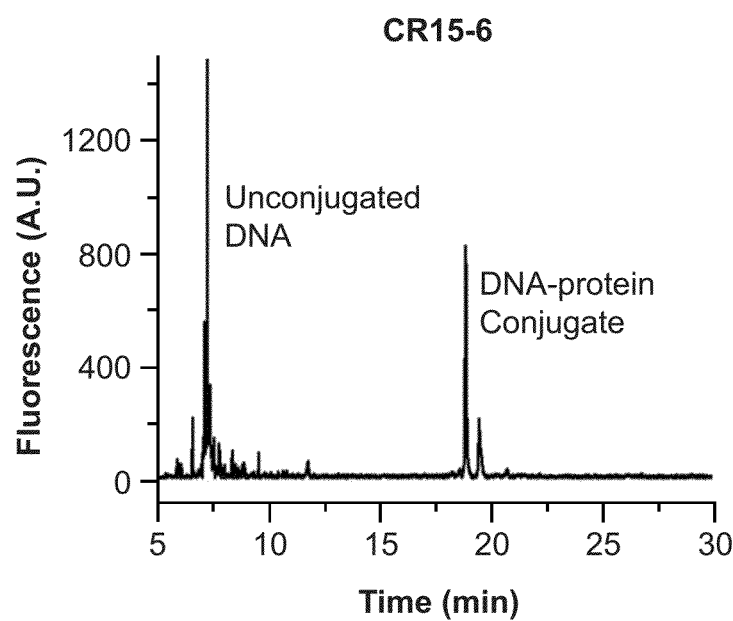
FIG. 10 depicts the results of a free-solution capillary electrophoresis analysis of drag-tag-DNA conjugates for the "CR15-6" preparation of protein polymer drag-tags (195 amino acids long, comprising a total of 12 arginines, so with a net, formal electrostatic charge of +11) without the His tag, using a 30-base ssDNA oligomer. As above, ABI 3100 CAE instrument, 36-cm array with 50 μm ID capillaries, 0.5×TTE, 7M urea, 5% (v/v) POP-6™, 1 kV/1 second injection, 310 V/cm, 55° C.

The cleaved CR15-6 protein was conjugated to a 30-nt ssDNA oligomer and analyzed by FSCE to determine its monodispersity and suitability as a drag-tag for free-solution DNA sequencing. The electropherogram is shown in FIG. 10. The "free" (unconjugated) DNA elutes first and corresponds to the peak on the far left of the electropherogram. The DNA-drag-tag conjugate elutes later due to the additional hydrodynamic drag from the drag-tag (larger peaks on the far right of FIG. 10). Although CR15-6 is about three quarters the size of the protein polymer drag-tag PC-36 (195- vs 267-aa), it showed comparable drag to PC-36 when analyzed with an attached ssDNA in FSCE as seen by a similar elution time of the DNA-drag-tag conjugate. The smaller size of CR15-6 is compensated for by the increased number of arginine residues (12 Arg in CR15-6 compared to 4 Arg in PC-36), indicating that increased hydrodynamic drag can be achieved without greatly increasing the protein size by intentionally including positive charges in the drag-tag sequence.

The extra peaks observed in FIG. 4 that are clustered around the DNA-protein conjugate peak indicate the heterogeneity of CR15-6. A two-peak pattern is seen in MALDI-TOF for CR15-6 after endoproteinase GluC digestion which suggests that at least some of the polydispersity is likely caused by the His tag removal step. The endoproteinase GluC digestion was performed at pH 8.5, where a deamidation reaction is possible at the two Gln residues in the T7 tag that changes Gln into Glu, the residue that is recognized and cleaved by endoproteinase GluC. Thus, the cleavage product can contain two different components: the protein polymer with the full length T7 tag and the protein polymer without the first eight residues of the T7 tag. This assumption is supported by the mass differences shown in the MALDI-TOF result.

E. Polypeptides Generated by Intein-Mediated Purification System

Although endoproteinase GluC showed good cleavage specificity for certain sequences and lengths of protein polymers, polydispersity remained an issue when treating other protein polymers (e.g., the two-peak pattern for CR15-6). However, keeping the C-terminal affinity tag attached to the protein polymers leads to low conjugation efficiency as the His tag can react with the sulfo-SMCC, accelerating the hydrolysis of the heterobifunctional linker during the conjugation step. Considering these limitations of the enzymatic cleavage method, an alternative method with better and more consistent results for obtaining monodisperse proteins is required. An intein-mediated purification system was chosen for its simple and highly efficient method of obtaining purified recombinant proteins. Additionally, it does not require an expensive enzyme like the GluC method, and it decreases the number of steps in the purification protocol.

A commercially available intein vector from New England Biolabs can be used to fuse a tag combining intein and a chitin binding domain (CBD) to the target protein. During affinity purification with chitin beads, a reducing reagent such as dithiothreitol (DTT) induces specific self-cleavage at the C-terminus of the first cysteine in the protein-tag junction, releasing the target protein from the chitin-bound intein tag. The absence of cysteine in the drag-tag sequences ensures high specificity and efficiency of DTT-induced self-cleavage. With the two steps of affinity purification and tag cleavage combined into one, the intein-mediated purification system minimizes the potential for material loss or protein degradation that may occur with the previously described, more complicated purification method.

The C-terminal intein-tag vector pTXB1 was chosen to prevent polydispersity of the protein polymers caused by premature protein truncations. The vector was modified as described earlier to adapt to the controlled cloning system. Gene R15-6 was inserted into MpTXB1 and expressed in *E. coli* BLR (DE3) cells with a induction temperature of 16° C. for 20 hours. The new protein (182 amino acids) expressed and purified in the intein system was designated IR15-6. No T7-tag was included in IR15-6 as it did not show a significant improvement in expression yield for fusion proteins. A lower concentration of NaCl in the column buffer was used as well as an additional 2 hour mixing step of the cell extract and prepared chitin beads at 4° C. for tighter binding between the CBD and the chitin beads. Overnight on-column cleavage was conducted at 25° C. with 50 mM DTT to achieve optimal cleavage results. Successful on-column cleavage and tag-free target protein was confirmed by SDS-PAGE, but visible amounts of co-eluted intein-CBD tag could still be observed with target protein polymers in the elution fractions. Preparative RP-HPLC on a C18 column was used as a second purification step to remove hydrophobic impurities from hydrophilic protein polymers. The same intein expression and purification strategy was applied to another gene, R18-3, and the resultant 110-aa protein polymer was designated IR18-3. MALDI-TOF confirmed the molecular masses of these two proteins after secondary purification by RP-HPLC. About 2-5 mg of protein polymer was obtained from one liter of expression culture after RP-HPLC purification.

Figure 11A:
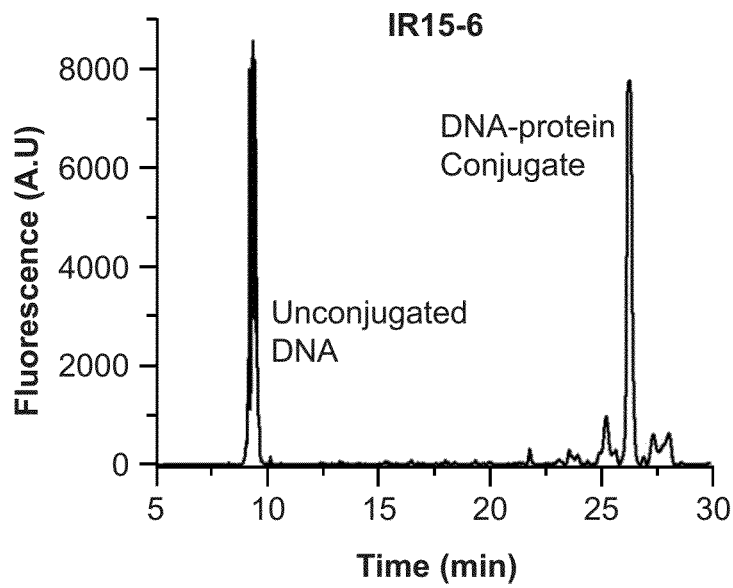
FIGS. 11A and 11B depict (11A) free-solution capillary electrophoresis of drag-tag-DNA conjugates for the IR15-6 protein polymer drag-tag (182 amino acids, 12 Arg) using a 30-base ssDNA oligomer. (11B) Free-solution capillary electrophoresis of DNA-drag-tag conjugate for IR18-3 (110 amino acids, 6 Arg) using a 30-base ssDNA oligomer. ABI 3100, 36-cm array with 50 μM ID capillaries, 1×TTE, 7M urea, 0.5% (v/v) POP-6™ (for dynamic coating), 1 kV/20 second injection, 310 V/cm, 55° C.
Figure 11B:
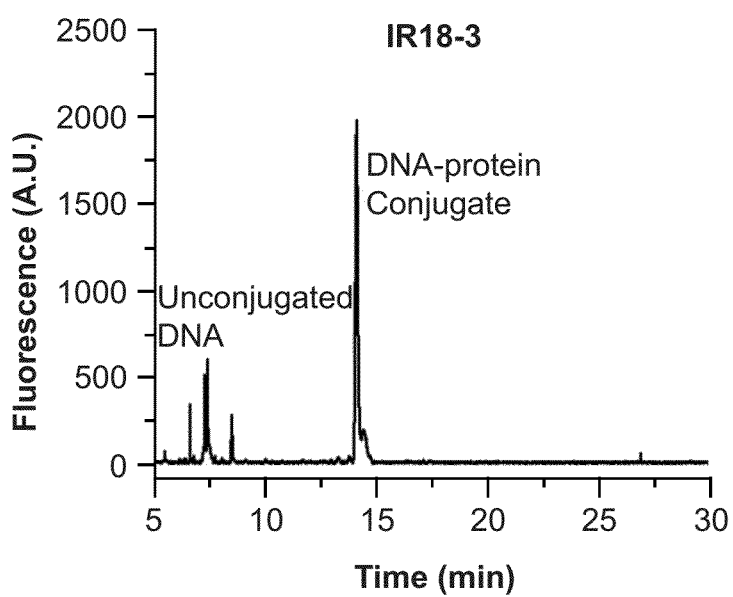

F. Characterization of Protein Polymers Generated from Intein-Mediated Purification System by FSCE The tag-free protein polymer drag-tags IR15-6 and IR18-3 were conjugated to a 30-nt ssDNA oligomer via the heterobifunctional linker molecule sulfo-SMCC and then analyzed by FSCE. FIG. 11 shows a mostly clean single peak with a strong signal for both DNA-drag-tag bioconjugates, demonstrating protein monodispersity and efficient conjugation reactions. Due to the smaller size and lower number of arginine residues (only 6 Arg in IR18-3), IR18-3 provides less drag than IR15-6. Although IR15-6 is slightly smaller than GluC-cleaved CR15-6 due to the absence of a T7-tag at the N-terminus, it shows larger effective drag than CR15-6 (FIG. 10) in FSCE separations as is seen by comparing the elution times of the DNA-drag-tag conjugate. The increased drag of IR15-6 compared to CR15-6 is likely due to the lack of the negatively charged C-terminal Glu, which causes the net charge of IR15-6 to be one higher than that of CR15-6.

G. FSCE Sequencing with an Intein-Purified Protein Polymer

Figure 12A:
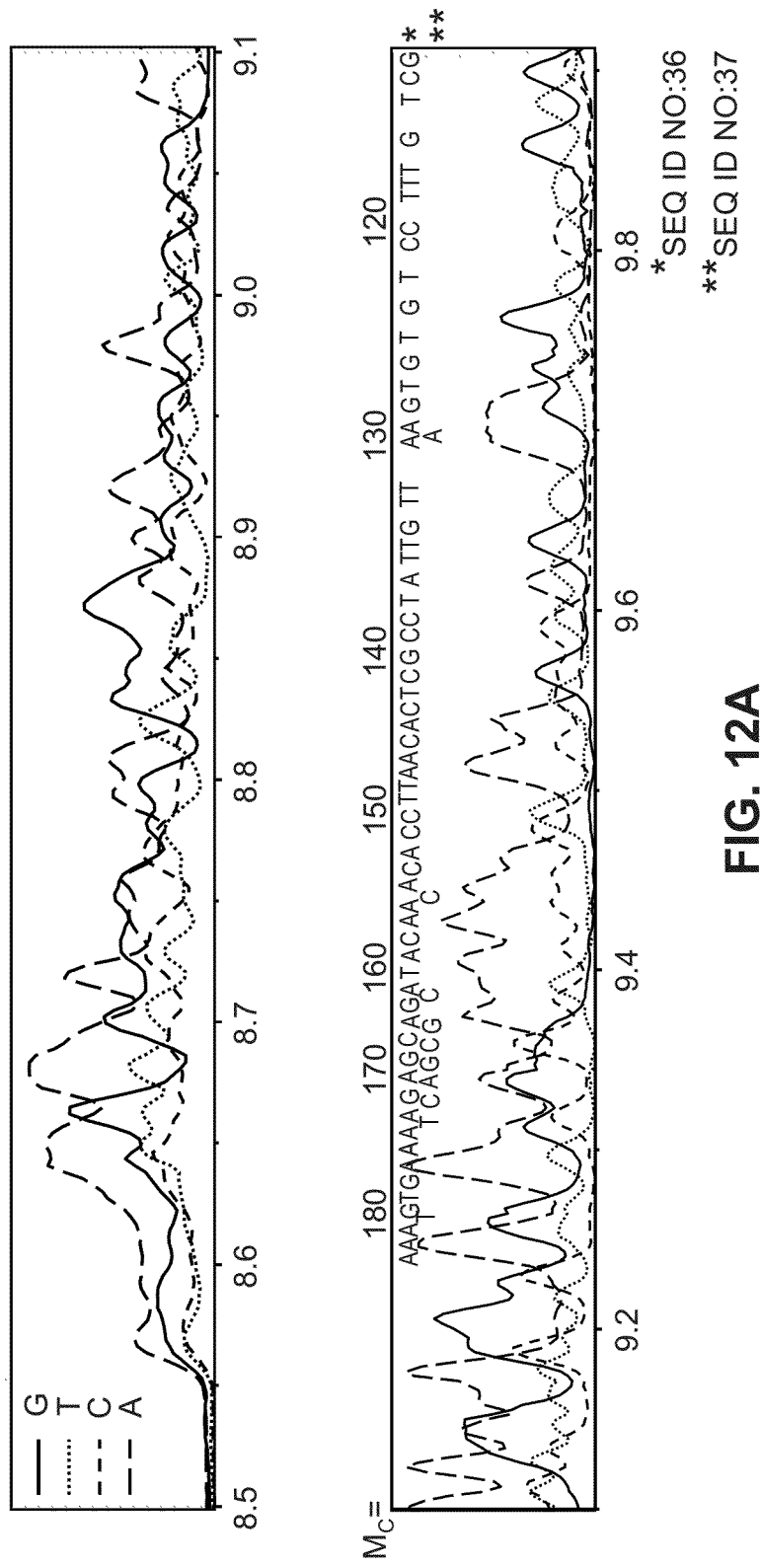
FIGS. 12A and 12B depict the sequencing separation of Sanger single-stranded, denatured DNA fragments coupled to the IR18-3 protein polymer drag-tag (110 aa, 6 Arg). The shortest DNA fragments elute last, and thus the DNA sequence is "read" backwards, from the right side of the bottom panel. ABI 3100, 36-cm capillary array with 50 μM ID capillaries, 1×TTE, 7M urea, 0.5% (v/v) POP-6™ (for dynamic coating), 1 kV/20 second injection, 287 V/cm, 55° C.
Figure 12B:
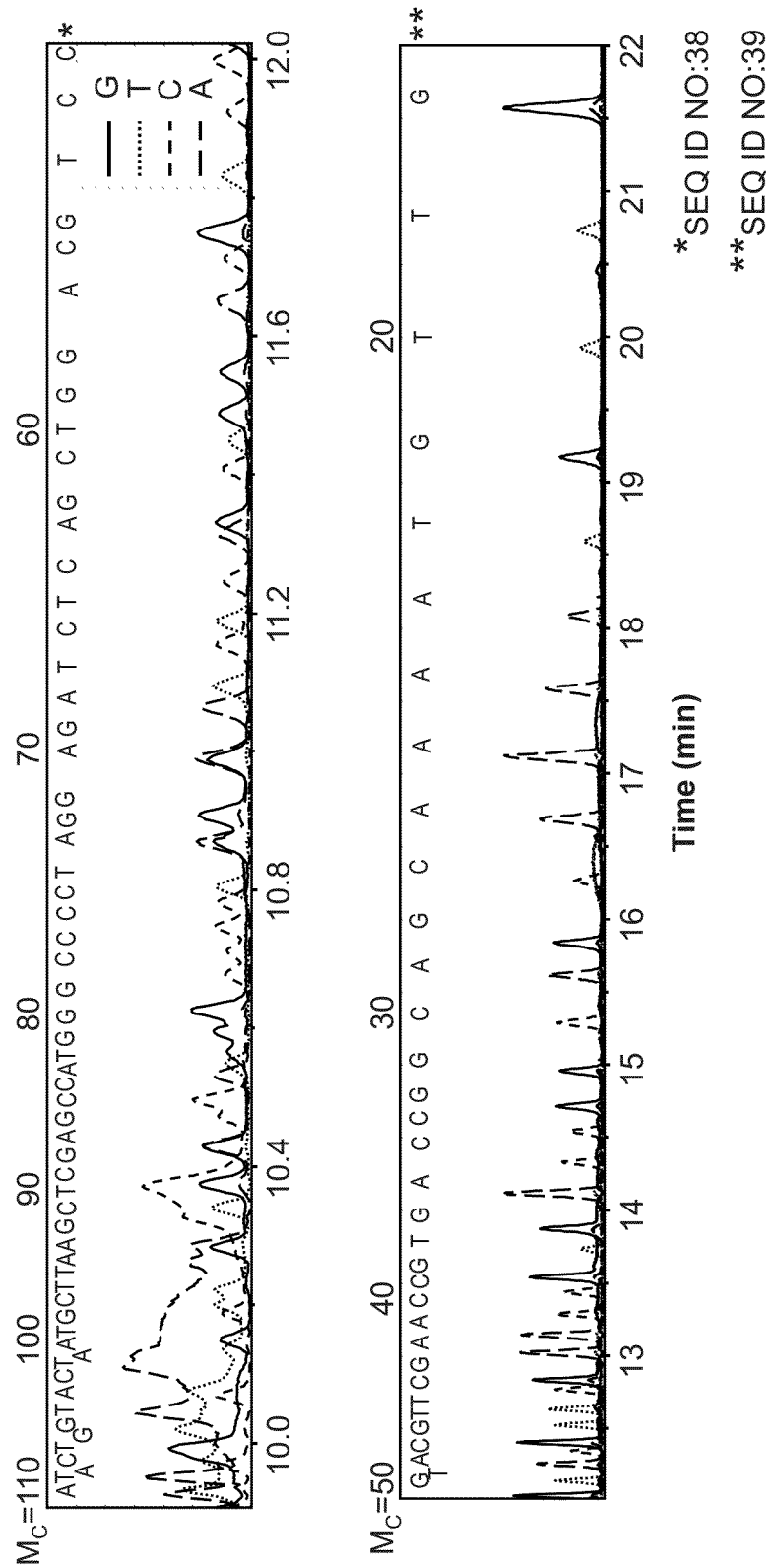

Sanger sequencing reactions were performed using either IR18-3 or IR15-6 conjugated to the sequencing primer prior to the extension reaction. The sequencing fragments were separated by free-solution electrophoresis without any entangled polymer network present. The raw electropherogram (without corrections that normalize peak heights or mobility shifts induced by different dyes) for sequencing with the IR18-3 drag-tag is shown in FIG. 12. Unlike traditional gel electrophoresis separations, in FSCE, the smaller fragments migrate slower than the larger ones; thus the sequencing data is "read" starting from the lower right corner of the figure and going "backwards" to the upper left corner. When using the known sequence of the M13mp18 template for alignment, the sequencing data obtained by IR18-3 can be read to around 180 bases. The read length is comparable to the sequencing data generated by the previously reported 127-aa drag-tag, a protein polymer drag-tag larger in size but with only two Arg. This result further confirmed that deliberately introducing some positive charges into the drag-tag sequences is another way to obtain higher drag for longer sequencing read lengths in FSCE besides simply increasing the size of the protein. Although IR18-3 showed a clean single peak when characterized by FSCE, there was a minor peak present in addition to the main peak in the single-base extension test, which may have caused increased peak widths in the sequencing separation.

No sequencing data was generated by the IR15-6-conjugated sequencing primer. Similar to the 390-aa and 516-aa protein polymers from the previous family of protein polymer drag-tags, enzymatic extension reactions appeared to be inhibited by the presence of the IR15-6 (182-aa) drag-tag on the 5' end of the sequencing fragment. The 182-aa long IR15-6, with 12 positively charged arginine residues, may have enough charge to interact strongly with either the sequencing primer or the ssDNA M13mp18 template. It is contemplated that an alternative conjugation method for appending protein drag-tags to Sanger fragments may avoid the inhibition described above.

All patents and patent publications referred to herein are hereby incorporated by reference in their entirety.

Certain modifications and improvements will occur to those skilled in the art upon a reading of the foregoing description. It should be understood that all such modifications and improvements have been deleted herein for the sake of conciseness and readability but are properly within the scope of the following claims.

What is claimed is:

1. A method for preparing a substantially monodisperse random coil polypeptide preparation comprising a plurality of random coil polypeptides, the method comprising the steps:
   a) expressing a random coil polypeptide precursor consisting of the random coil polypeptide and a C-terminal affinity tag using a plasmid expression vector which comprises a nucleic acid sequence which encodes the random coil polypeptide precursor, wherein the precursor comprises the random coil polypeptide linked at its C-terminus to the C-terminal affinity tag via an intein domain or a GluC cleavage site consisting of the sequence IEGR (SEQ ID NO:22), wherein the random coil polypeptide has an electrostatic charge less than +18, and wherein the random coil polypeptide comprises repeating amino acid sequences of 30-250, wherein each of repeating sequences comprises amino acids independently selected from glycine, alanine, threonine, serine, and arginine;

b) contacting the expressed polypeptide precursor with an affinity column having affinity for the C-terminal tag;

c) completely cleaving the affinity tag by exposing the expressed polypeptide precursor to endoproteinase GluC that cleaves within said GluC cleavage site, or exposing to dithiothreitol which induces the intein domain's self-cleavage; and d) purifying the random coil polypeptide from which the affinity tag has been completely cleaved off by column chromatography thereby preparing plurality of substantially monodisperse random coil polypeptide preparation;

wherein the degree of the monodispersity of the plurality of random coil polypeptides after removal of the C-terminal affinity tag is much greater than the degree of the monodispersity of corresponding polypeptides which are obtained after the cleavage of the affinity tag from the precursor consisting of the random coil polypeptide and the affinity tag at its N-terminus of said polypeptide, and wherein the monodispersity is determined by free-solution conjugate electrophoresis.

2. The method of claim 1, wherein the polypeptide is expressed in *E. coli*.

3. A substantially monodisperse random coil polypeptide made by the method of claim 1.

4. The method of claim 1, wherein the polypeptide has at least 10 of the repeating sequences wherein each repeating sequence has at least five amino acids.

5. The method of claim 1, wherein the polypeptide has 30 to 70 of the repeating sequences wherein each repeating sequence has at least seven amino acids.

6. The method of claim 1, wherein each of the repeating sequences is selected from GAGTGSA (SEQ ID NO: 1) and GAGTGRA (SEQ ID NO: 2).

7. The method of claim 1, wherein the polypeptide comprises at its N-terminus a T7 tag comprising the amino acid sequence MASMTGGQQMG (SEQ ID NO: 3).

8. The method of claim 1, wherein when the C-terminal tag is not an intein, the polypeptide is greater than 250 amino acids in length.

9. The method of claim 1, wherein the polypeptide further comprises a second non-identical repeating amino sequence.

10. The method of claim 1, wherein the polypeptide comprises, on average, evenly spaced arginines.

11. The method of claim 1, wherein the arginines are spaced every 18 amino acids, on average.

12. The method of claim 1, wherein the affinity tag is a polyhistidine tag.

13. The method of claim 1, wherein the random coil polypeptide has 30 to 70 repeats of the repeating amino acid sequence, wherein the amino acid sequence is GAGTGSA (SEQ ID NO: 1) and GAGTGRA (SEQ ID NO: 2).

14. The method of claim 1, wherein the random coil polypeptide is less than 250 amino acids in length and each of the repeating amino acid sequences is 7 amino acids in length.

15. The method of claim 1, wherein the plurality of random coil polypeptides in the preparation are at least 95% identical to each other.

16. The method of claim 1, wherein the plurality of random coil polypeptides in the preparation are at least 99% identical to each other.

* * * * *

SEQUENCE LISTING

<160> NUMBER OF SEQ ID NOS: 28

<210> SEQ ID NO 1
<211> LENGTH: 7
<212> TYPE: PRT
<213> ORGANISM: Artificial Sequence
<220> FEATURE:
<223> OTHER INFORMATION: laboratory made peptide

<400> SEQUENCE: 1

Gly Ala Gly Thr Gly Ser Ala
1               5

<210> SEQ ID NO 2
<211> LENGTH: 7
<212> TYPE: PRT
<213> ORGANISM: Artificial Sequence
<220> FEATURE:
<223> OTHER INFORMATION: laboratory made

<400> SEQUENCE: 2

Gly Ala Gly Thr Gly Arg Ala
1               5

<210> SEQ ID NO 3
<211> LENGTH: 11
<212> TYPE: PRT
<213> ORGANISM: Artificial Sequence
<220> FEATURE:
<223> OTHER INFORMATION: laboratory made

<400> SEQUENCE: 3

Met Ala Ser Met Thr Gly Gly Gln Gln Met Gly
1               5                   10

<210> SEQ ID NO 4
<211> LENGTH: 126
<212> TYPE: PRT
<213> ORGANISM: Artificial Sequence
<220> FEATURE:
<223> OTHER INFORMATION: laboratory made

<400> SEQUENCE: 4

Gly Ala Gly Thr Gly Ser Ala Gly Ala Gly Thr Gly Ser Ala Gly Ala
1               5                   10                  15

Gly Thr Gly Ser Ala Gly Ala Gly Thr Gly Ser Ala Gly Ala Gly Thr
            20                  25                  30

Gly Arg Ala Gly Ala Gly Thr Gly Ser Ala Gly Ala Gly Thr Gly Ser
        35                  40                  45

Ala Gly Ala Gly Thr Gly Ser Ala Gly Ala Gly Thr Gly Ser Ala Gly
    50                  55                  60

Ala Gly Thr Gly Ser Ala Gly Ala Gly Thr Gly Ser Ala Gly Ala Gly
65                  70                  75                  80

Thr Gly Ser Ala Gly Ala Gly Thr Gly Arg Ala Gly Ala Gly Thr Gly
                85                  90                  95

Ser Ala Gly Ala Gly Thr Gly Ser Ala Gly Ala Gly Thr Gly Ser Ala
            100                 105                 110

Gly Ala Gly Thr Gly Ser Ala Gly Ala Gly Thr Gly Ser Ala
        115                 120                 125

<210> SEQ ID NO 5
<211> LENGTH: 40
<212> TYPE: DNA
<213> ORGANISM: Artificial Sequence
<220> FEATURE:
<223> OTHER INFORMATION: laboratory made

<400> SEQUENCE: 5
cttgaagaaa aatatgagga gcatttgtat gagcgcgatg                                40

```
<210> SEQ ID NO 6
<211> LENGTH: 27
<212> TYPE: DNA
<213> ORGANISM: Artificial Sequence
<220> FEATURE:
<223> OTHER INFORMATION: laboratory made

<400> SEQUENCE: 6
gaggaagcgg aagagagcct gatgcgg                                        27

<210> SEQ ID NO 7
<211> LENGTH: 48
<212> TYPE: DNA
<213> ORGANISM: Artificial Sequence
<220> FEATURE:
<223> OTHER INFORMATION: laboratory made

<400> SEQUENCE: 7
attcccctct agaaataatt ttgtttaact ttaagaagga gatatacc                 48

<210> SEQ ID NO 8
<211> LENGTH: 56
<212> TYPE: DNA
<213> ORGANISM: Artificial Sequence
<220> FEATURE:
<223> OTHER INFORMATION: laboratory made

<400> SEQUENCE: 8
caccagtcat gctagccatg gtatatctcc ttcttaaagt taaacaaaat tatttc        56

<210> SEQ ID NO 9
<211> LENGTH: 47
<212> TYPE: DNA
<213> ORGANISM: Artificial Sequence
<220> FEATURE:
<223> OTHER INFORMATION: laboratory made

<400> SEQUENCE: 9
ggctagcatg actggtggac agcaaatggg ttgaagagcg tacatca                  47

<210> SEQ ID NO 10
<211> LENGTH: 48
<212> TYPE: DNA
<213> ORGANISM: Artificial Sequence
<220> FEATURE:
<223> OTHER INFORMATION: laboratory made

<400> SEQUENCE: 10
ccgccagacc tgaagagccg tgcacatatg atgtacgctc ttcaaccc                 48

<210> SEQ ID NO 11
<211> LENGTH: 50
<212> TYPE: DNA
<213> ORGANISM: Artificial Sequence
<220> FEATURE:
<223> OTHER INFORMATION: laboratory made

<400> SEQUENCE: 11
gctcttcagg tgcggccgca catcatcatc atcatcatca tcactaagga               50

<210> SEQ ID NO 12
<211> LENGTH: 49
<212> TYPE: DNA
<213> ORGANISM: Artificial Sequence
<220> FEATURE:
<223> OTHER INFORMATION: laboratory made
```

```
<400> SEQUENCE: 12
gacatctcga gcgttaggat ccttagtgat gatgatgatg atgatgatg              49

<210> SEQ ID NO 13
<211> LENGTH: 34
<212> TYPE: DNA
<213> ORGANISM: Artificial Sequence
<220> FEATURE:
<223> OTHER INFORMATION: laboratory made

<400> SEQUENCE: 13
attcccctct agaaataatt tgtttaact ttaa                              34

<210> SEQ ID NO 14
<211> LENGTH: 21
<212> TYPE: DNA
<213> ORGANISM: Artificial Sequence
<220> FEATURE:
<223> OTHER INFORMATION: laboratory made

<400> SEQUENCE: 14
gacatctcga gcgttaggat c                                           21

<210> SEQ ID NO 15
<211> LENGTH: 76
<212> TYPE: DNA
<213> ORGANISM: Artificial Sequence
<220> FEATURE:
<223> OTHER INFORMATION: laboratory made

<400> SEQUENCE: 15
caggtgcggc cgcaatcgag ggaaggcatc atcatcatca tcatcatcac taaggatcct  60
aacgctcgag caccac                                                 76

<210> SEQ ID NO 16
<211> LENGTH: 267
<212> TYPE: PRT
<213> ORGANISM: Artificial Sequence
<220> FEATURE:
<223> OTHER INFORMATION: laboratory made

<400> SEQUENCE: 16
```

Ala Ser Met Thr Gly Gly Gln Gln Met Gly Ala Gly Thr Gly Ser Ala
1               5                   10                  15

Gly Ala Gly Thr Gly Ser Ala Gly Ala Gly Thr Gly Ser Ala Gly Ala
            20                  25                  30

Gly Thr Gly Ser Ala Gly Ala Gly Thr Gly Arg Ala Gly Ala Gly Thr
        35                  40                  45

Gly Ser Ala Gly Ala Gly Thr Gly Ser Ala Gly Ala Gly Thr Gly Ser
    50                  55                  60

Ala Gly Ala Gly Thr Gly Ser Ala Gly Ala Gly Thr Gly Ser Ala Gly
65                  70                  75                  80

Ala Gly Thr Gly Ser Ala Gly Ala Gly Thr Gly Ser Ala Gly Ala Gly
                85                  90                  95

Thr Gly Arg Ala Gly Ala Gly Thr Gly Ser Ala Gly Ala Gly Thr Gly
            100                 105                 110

Ser Ala Gly Ala Gly Thr Gly Ser Ala Gly Ala Gly Thr Gly Ser Ala
        115                 120                 125

Gly Ala Gly Thr Gly Ser Ala Gly Ala Gly Thr Gly Ser Ala Gly Ala
    130                 135                 140

```
Gly Thr Gly Ser Ala Gly Ala Gly Thr Gly Ser Ala Gly Ala Gly Thr
145                 150                 155                 160
Gly Ser Ala Gly Ala Gly Thr Gly Arg Ala Gly Ala Gly Thr Gly Ser
                165                 170                 175
Ala Gly Ala Gly Thr Gly Ser Ala Gly Ala Gly Thr Gly Ser Ala Gly
            180                 185                 190
Ala Gly Thr Gly Ser Ala Gly Ala Gly Thr Gly Ser Ala Gly Ala Gly
        195                 200                 205
Thr Gly Ser Ala Gly Ala Gly Thr Gly Ser Ala Gly Ala Gly Thr Gly
    210                 215                 220
Arg Ala Gly Ala Gly Thr Gly Ser Ala Gly Ala Gly Thr Gly Ser Ala
225                 230                 235                 240
Gly Ala Gly Thr Gly Ser Ala Gly Ala Gly Thr Gly Ser Ala Gly Ala
                245                 250                 255
Gly Thr Gly Ser Ala Gly Ala Ala Ile Glu
                260                 265
```

<210> SEQ ID NO 17
<211> LENGTH: 5
<212> TYPE: PRT
<213> ORGANISM: Artificial Sequence
<220> FEATURE:
<223> OTHER INFORMATION: laboratory made

<400> SEQUENCE: 17

```
Asp Asp Asp Asp Lys
1               5
```

<210> SEQ ID NO 18
<211> LENGTH: 23
<212> TYPE: DNA
<213> ORGANISM: Artificial Sequence
<220> FEATURE:
<223> OTHER INFORMATION: laboratory made

<400> SEQUENCE: 18
gcatgtatct atcatccatc tct                                          23

<210> SEQ ID NO 19
<211> LENGTH: 30
<212> TYPE: DNA
<213> ORGANISM: Artificial Sequence
<220> FEATURE:
<223> OTHER INFORMATION: laboratory made

<400> SEQUENCE: 19 cctttaggg ttttcccagt cacgacgttg                                    30

<210> SEQ ID NO 20
<211> LENGTH: 8
<212> TYPE: PRT
<213> ORGANISM: Artificial Sequence
<220> FEATURE:
<223> OTHER INFORMATION: laboratory made

<400> SEQUENCE: 20

```
Asp Tyr Lys Asp Asp Asp Asp Lys
1               5
```

<210> SEQ ID NO 21
<211> LENGTH: 8
<212> TYPE: PRT
<213> ORGANISM: Artificial Sequence

```
<220> FEATURE:
<223> OTHER INFORMATION: laboratory made

<400> SEQUENCE: 21

Trp Ser His Pro Gln Phe Glu Lys
1               5

<210> SEQ ID NO 22
<211> LENGTH: 4
<212> TYPE: PRT
<213> ORGANISM: Artificial Sequence
<220> FEATURE:
<223> OTHER INFORMATION: factor Xa cleave site

<400> SEQUENCE: 22

Ile Glu Gly Arg
1

<210> SEQ ID NO 23
<211> LENGTH: 17
<212> TYPE: DNA
<213> ORGANISM: Artificial Sequence
<220> FEATURE:
<223> OTHER INFORMATION: laboratory made

<400> SEQUENCE: 23
gttttcccag tcacgac                                                    17

<210> SEQ ID NO 24
<211> LENGTH: 180
<212> TYPE: PRT
<213> ORGANISM: Artificial Sequence
<220> FEATURE:
<223> OTHER INFORMATION: laboratory made

<400> SEQUENCE: 24

Gly Thr Ala Gly Ser Ala Thr Gly Ala Gly Ser Ala Gly Ser Arg Gly
1               5                   10                  15

Thr Ala Gly Ser Gly Ala Thr Gly Ala Ser Gly Thr Gly Arg Gly Thr
            20                  25                  30

Ala Gly Ser Ala Thr Gly Ala Gly Ser Ala Gly Ser Arg Gly Thr Ala
        35                  40                  45

Gly Ser Gly Ala Thr Gly Ala Ser Gly Thr Gly Arg Gly Thr Ala Gly
    50                  55                  60

Ser Ala Thr Gly Ala Gly Ser Ala Gly Ser Arg Gly Thr Ala Gly Ser
65                  70                  75                  80

Gly Ala Thr Gly Ala Ser Gly Thr Gly Arg Gly Thr Ala Gly Ser Ala
                85                  90                  95

Thr Gly Ala Gly Ser Ala Gly Ser Arg Gly Thr Ala Gly Ser Gly Ala
            100                 105                 110

Thr Gly Ala Ser Gly Thr Gly Arg Gly Thr Ala Gly Ser Ala Thr Gly
        115                 120                 125

Ala Gly Ser Ala Gly Ser Arg Gly Thr Ala Gly Ser Gly Ala Thr Gly
    130                 135                 140

Ala Ser Gly Thr Gly Arg Gly Thr Ala Gly Ser Ala Thr Gly Ala Gly
145                 150                 155                 160

Ser Ala Gly Ser Arg Gly Thr Ala Gly Ser Gly Ala Thr Gly Ala Ser
                165                 170                 175

Gly Thr Gly Arg
            180
```

```
<210> SEQ ID NO 25
<211> LENGTH: 108
<212> TYPE: PRT
<213> ORGANISM: Artificial Sequence
<220> FEATURE:
<223> OTHER INFORMATION: laboratory made

<400> SEQUENCE: 25

Gly Thr Ala Gly Ser Ala Gly Thr Ala Gly Ser Ala Thr Ala Gly
1               5                   10                  15

Ser Ala Gly Ser Arg Gly Thr Ala Gly Ser Gly Ala Thr Gly Ala Ser
                20                  25                  30

Gly Thr Gly Arg Gly Thr Ala Gly Ser Ala Gly Thr Ala Gly Ser Ala
            35                  40                  45

Thr Gly Ala Gly Ser Ala Gly Ser Arg Gly Thr Ala Gly Ser Gly Ala
    50                  55                  60

Thr Gly Ala Ser Gly Thr Gly Arg Gly Thr Ala Gly Ser Ala Gly Thr
65              70                  75                  80

Ala Gly Ser Ala Thr Gly Ala Gly Ser Ala Gly Ser Arg Gly Thr Ala
                85                  90                  95

Gly Ser Gly Ala Thr Gly Ala Ser Gly Thr Gly Arg
            100                 105

<210> SEQ ID NO 26
<211> LENGTH: 54
<212> TYPE: DNA
<213> ORGANISM: Artificial Sequence
<220> FEATURE:
<223> OTHER INFORMATION: laboratory made

<400> SEQUENCE: 26
catatgggtt gaagagccgt acatgagctc tgcacgggct cttcaggtgc gtgc        54

<210> SEQ ID NO 27
<211> LENGTH: 49
<212> TYPE: DNA
<213> ORGANISM: Artificial Sequence
<220> FEATURE:
<223> OTHER INFORMATION: laboratory made

<400> SEQUENCE: 27 tatggggttga agagccgtac atgagctctg cacgggctct tcaggtgcg             49

<210> SEQ ID NO 28
<211> LENGTH: 50
<212> TYPE: DNA
<213> ORGANISM: Artificial Sequence
<220> FEATURE:
<223> OTHER INFORMATION: laboratory made

<400> SEQUENCE: 28
gcacgcacct gaagagcccg tgcagagctc atgtacggct cttcaaccca            50
```